(12) United States Patent
Van Eyk et al.

(10) Patent No.: US 8,232,066 B2
(45) Date of Patent: Jul. 31, 2012

(54) PEPTIDE ANTIBODY DEPLETION AND ITS APPLICATION TO MASS SPECTROMETRY SAMPLE PREPARATION

(75) Inventors: Jennifer E. Van Eyk, Baltimore, MD (US); David Raymond Graham, Baltimore, MD (US); Rebekah Lynn Gundry, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 643 days.

(21) Appl. No.: 12/307,510

(22) PCT Filed: Jul. 3, 2007

(86) PCT No.: PCT/US2007/015390
§ 371 (c)(1),
(2), (4) Date: Jun. 12, 2009

(87) PCT Pub. No.: WO2008/005455
PCT Pub. Date: Jan. 10, 2008

(65) Prior Publication Data
US 2010/0047812 A1  Feb. 25, 2010

Related U.S. Application Data

(60) Provisional application No. 60/818,363, filed on Jul. 3, 2006.

(51) Int. Cl.
*G01N 31/00* (2006.01)
*G01N 33/53* (2006.01)

(52) U.S. Cl. ........ 435/7.21; 435/7.1; 436/501; 436/518; 424/91; 424/520; 422/50; 530/300; 530/350

(58) Field of Classification Search .................. None
See application file for complete search history.

(56) References Cited

U.S. PATENT DOCUMENTS
2002/0055186 A1  5/2002  Barry et al.

FOREIGN PATENT DOCUMENTS
WO  WO 2004/031730 A2  4/2004
WO  WO 2005/049653 A1  6/2005

OTHER PUBLICATIONS

Kuster B et al: "Scoring proteomes with proteotypic peptide probes." Nature Rev. Mol Cell Biol, vol. 6, No. 7, Jul. 2005, pp. 577-583.
Zhang F et al: "Quantitation of human glutathione S-transferases in complex matrices by liquid chromatography/tandem mass spectrometry with signature peptides" Rapid Commun Mass Spectrom, vol. 18, No. 4, Feb. 29, 2004, pp. 491-498.
Steele L F et al: "Efficient and specific removal of albumin from human serum samples" Mol Cell Proteom, vol. 2, No. 4, 2003 pp. 262-270.
Doyen N et al: "Study of the antigenic structure of human serum albumin with monoclonal antibodies." Mol Immunol, vol. 22, No. 1, Jan. 1985, pp. 1-10.

*Primary Examiner* — Lisa Cook
(74) *Attorney, Agent, or Firm* — Johns Hopkins Technology Transfer

(57) ABSTRACT

The present invention relates, e.g., to a method for pre-processing a sample for mass spectral analysis, comprising cleaving proteins in the sample to peptides and immunodepleting highly abundant and/or well-ionizing and/or proteotypic peptides from the sample. Also described are methods for identifying well-ionizing peptides for use in this and other methods; analytic (diagnostic) methods using antibodies against highly ionizable peptides from a protein target of interest; and compositions kits and devices comprising antibodies of the invention.

19 Claims, 3 Drawing Sheets

PEPTIDE ANTIBODY DEPLETION AND ITS APPLICATION TO MASS SPECTROMETRY SAMPLE PREPARATION

This application is a U.S. National Stage of International Application No. PCT/US2007/015390, filed Jul. 3, 2007, designating the United States and claiming priority from U.S. Provisional Application No. 60/818,363, filed Jul. 3, 2007, which is incorporated by reference herein in its entirety.

FIELD OF THE INVENTION

The present invention relates, e.g., to a method to prepare samples for mass spectral analysis.

BACKGROUND INFORMATION

In mass spectrometry (MS), the ability to detect all analytes present in a sample depends on a number of parameters, including the complexity of the sample mixture. Ideally, the goal in any MS experiment is to detect 100% of the analytes present. However, as sample complexity increases, the ability to detect all species present markedly decreases. This is due to several factors, including: (1) ionization suppression (seen in MALDI (matrix-assisted laser desorption/ionization spectroscopy), (2) differences in ionization potential (seen in MALDI and ESI (electrospray ionization mass spectroscopy) and (3) the fact that higher abundance species can drown out the lower abundance species due to the limited dynamic range of common detectors (seen in MALDI and ESI). In MS, an analyte (e.g. peptide, protein, lipid, etc) must become ionized in the sample source region in order for it to reach the detector. The potential for any analyte to become ionized (ionization potential) is related to the sequence of the peptide (e.g. number of charged residues) as well as the presence of other components in the sample mixture, since other peptides may compete for ionization and contaminant adducts (e.g. Na, K) can adversely affect the ionization efficiency. These challenges are problematic in the field of proteomics, where any one sample may contain hundreds of proteins present in concentrations that span the dynamic range of $10^9$ orders of magnitude (i.e. $10^8$ log difference in abundance from the lowest abundance protein to the highest abundance protein). When these samples are subjected to enzymatic or chemical digestion, the resulting peptide mixtures are considerably more complicated than the original protein mixtures. Consequently, the presence of high abundance proteins in a proteomics mixture can present challenges for the detection of lesser abundant proteins due to resulting dynamic range issues and competition for ionization.

In addition to the adverse effects of high abundance peptides on the ionization efficiency and detection of other peptides, the presence of peptides from contaminating proteins in a proteomics study can affect the random match probability for peptide mass fingerprinting (PMF). In PMF, the peptide masses from an enzymatic or chemical digestion of the protein are compared to the masses from an in silico digest of protein in a database, for the purpose of protein identification. Consequently, when contaminant peptide masses (from keratin or trypsin, for example) are present, they may cause random matching of experimental masses to the theoretical masses in the database if they are combined with peptide analyte masses in a single search. Thus, the presence of peptides from both high abundance proteins and contaminant proteins can have an adverse-affect on (1) the ability to obtain complete sequence coverage of the protein(s) of interest and (2) can interfere with the ability to correctly identify the analyte of interest.

In proteomics, two approaches are commonly used to overcome complications from high abundance proteins or interference from contaminant proteins. These include (1) removal of peptide masses attributed to contaminant/high abundance proteins from the peptide peak list prior to database searching, or alternatively, filtering out peptides attributed to the contaminant/high abundance proteins after the database search and (2) removal of high abundance proteins as a whole, by affinity depletion (or other) methods prior to enzymatic/chemical digestion. Unfortunately, the removal of peptide masses from the peak lists, either prior to or after database searching, does not address the fundamental issues of ionization suppression or saturation of the detector that occur during data acquisition. While this approach may simplify the database search and data analysis, it does not lead to an ability to actually detect any more peptides. Additionally, the removal of intact proteins prior to digestion is plagued by the problem that protein depletion methods can non-specifically remove other proteins in low abundance (or high abundance proteins if there are high affinity interactions). Therefore, the removal of intact higher abundance proteins is disadvantageous for studies that aim to identify as many proteins as possible in the original sample.

In diagnostic assays for proteins of interest, the primary limitation is the detection capabilities of the target of interest. The most sensitive assays currently in use are generally those employing Enzyme Linked Immuno-Sorbant Assay (ELISA), which uses an antibody to capture a target and then a secondary antibody coupled to an enzyme to allow for amplification of the detection signal. These assays typically allow for up to low picogram levels of detection.

DETAILED DESCRIPTION

Figure 1:
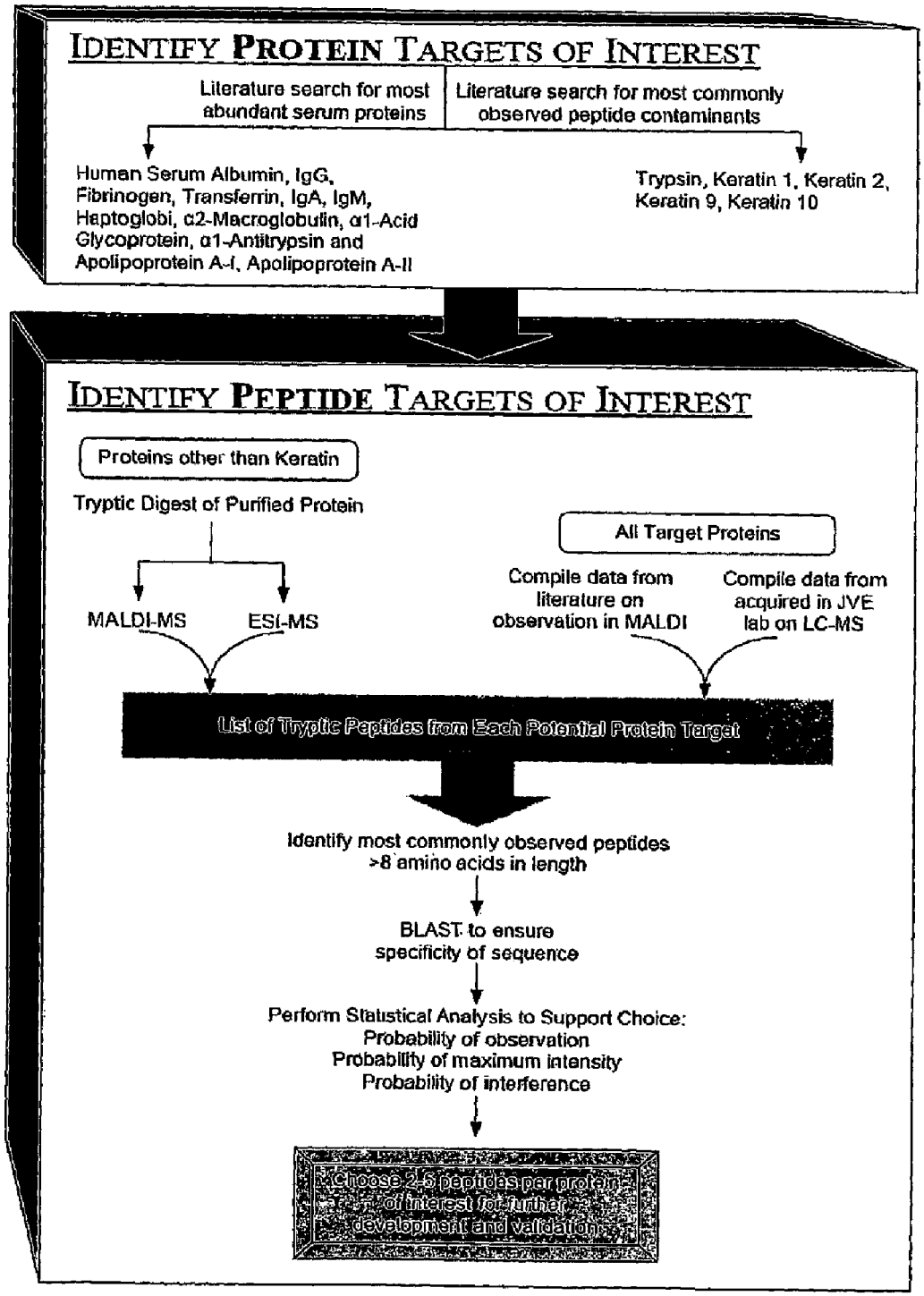
FIG. 1 shows diagrammatically Part II of the PAD development workflow.

The present inventors have recognized that an efficient, reproducible method for pre-processing protein-containing samples for mass spectral analysis (sometimes referred to herein as mass spec, mass spectrometry or mass spectroscopy) is to physically remove undesirable highly abundant and/or well-ionizing peptides from the samples before the analysis (data acquisition) is conducted. In one embodiment of the method, the peptides which are removed have been previously identified as being common contaminants in preparations for mass spec analysis. In another embodiment, peptides that are well-ionizing (either from highly abundant proteins, or from proteins that are lower in abundance, but wherein certain peptides are particularly well-ionizing and thus potentially problematic for MS analysis) are identified by a method as follows: one or more potentially contaminating proteins are cleaved to peptides with a protease or chemical method; the resulting peptides are subjected to MS; the peptides observed in the MS analysis are ranked in order with respect to ionization or ionizing potential (e.g., beginning with the most highly ionizing peptide); and, optionally, a suitable number of peptides (e.g. about 3-8 of the most well-ionized peptides for each protein) are selected, e.g. as targets for removal.

A variety of methods for physical removal of the highly abundant and/or well-ionizing peptides can be employed in a method of the invention. In one method, the peptides are immunodepleted from the sample to be analyzed. In such an embodiment, antibodies are generated against the peptides to be removed and, optionally, are attached to a surface (e.g. a chip, beads, pipette tips, etc.); the sample that is to be subjected to MS is contacted with the antibodies under conditions that are effective for the antibodies to bind to their cognate peptides; and the bound peptides are removed from the sample.

Advantages of this method include that, by removing peptides (e.g., well-ionizing peptides) derived from high abundance and/or common contaminating proteins, rather than by removing the full-length proteins, themselves, one can reduce or eliminate the removal of desirable peptides, such as peptides that are present in the sample in low amounts (low abundance peptides). Without wishing to be bound by any particular mechanism, it is suggested that, because protein: protein interactions are stabilized by secondary, tertiary and quaternary structure, by working at the peptide level, one can eliminate these higher order structures that could cause non-specific (or even specific) depletion of other proteins. Furthermore, by targeting peptides that are particularly well-ionizable, one can remove a source of many of the problems that limit MS analysis (e.g., ionization suppression and differences in ionization potential). By removing contaminating peptides from a sample destined for MS analysis, methods of the invention can impart a beneficial effect on the resulting spectrum, and can allow for efficient detection (coverage) of proteins/peptides, including of low abundance proteins/peptides. Such a method is particularly useful when analyzing peptide mixtures generated in proteomics analyses.

In another embodiment of the invention, antibodies are generated against highly ionizable peptides derived from a protein of interest (e.g. a protein from a pathogen of interest or a disease marker), by a method as described herein, but instead of using the antibodies to eliminate these peptides from a sample being processed for MS, the antibodies are used in order to isolate or concentrate the peptides and, subsequently, to detect the protein from which the highly ionized peptides were derived. For example, a sample suspected of containing a protein of interest (e.g., from a pathogen or disease marker) is cleaved to peptides and then contacted with one or more antibodies specific for highly ionizable peptides of the protein, under conditions that are effective to bind the highly ionizable peptides specifically to the antibodies, if the highly ionizable peptides are present in the mixture of cleaved proteins. Bound peptides are then separated from the mixture of peptides and are thus concentrated (enriched); and the concentrated peptides are eluted and analyzed by MS. The presence of the highly ionizable peptides in the readout indicates that the sample contained the protein of interest.

Advantages of such a detection method include, e.g., that, by focusing on the detection of highly ionizable peptides, one can attain a much higher sensitivity and specificity of detection by MS than by detecting less highly ionizable peptides. It is expected that the detection level will be essentially at the level of detection of the mass spectrometer (e.g. at the femtomolar level, or even at the attomolar level).

In addition to the methods discussed above, described herein are compositions comprising peptides of interest or antibodies specific for the peptides, and platforms (e.g., devices) comprising such compositions, bound to a solid surface (such as a bead, column, chip, etc.). Such compositions and devices can be used in methods of the invention. For example, such a device (sometimes referred to herein as a peptide antibody depletion device, or PAD) can be used to remove peptides from common protein contaminants, including proteins that are in high abundance in particular samples, such as serum proteins.

One aspect of the present invention is a method for pre-processing a sample for mass spectral analysis, comprising cleaving proteins in the sample to peptides and immunodepleting highly abundant and/or well-ionizing and/or proteotypic peptides from the sample.

The immunodepletion may be carried out, for example, by (a) contacting the peptides resulting from cleavage of the protein(s) with one or more antibodies that are specific for highly abundant and/or well-ionizing and/or proteotypic peptides in the sample, under conditions that are effective for the antibodies to bind specifically to their cognate peptides, and (b) removing the bound abundant and/or well-ionizing and/or proteotypic peptides from the sample.

Another aspect of the invention is a method for identifying highly ionizing peptides of a protein, comprising (a) cleaving the protein with a protease or a chemical method; (b) subjecting the resulting peptides to mass spectrometry; (c) ranking the peptides in order with respect to their ionization potential (e.g., beginning with the most highly ionizing peptides); and, optionally, (d) selecting about 3-8 of the most highly ionizing peptides from each protein.

As used herein, the singular forms "a," "an," and "the" include plural referents unless the context clearly dictates otherwise. For example, "a" protein, as used above, means one or more proteins, which can be the same or different.

In one embodiment of this method, the protein for which highly ionizing peptides are identified is a known or suspected contaminant, which can interfere with mass spectrophotometric analysis of a protein of interest in a sample. For example, this identification method allows an investigator to identify which (highly ionizable) peptides from a high abundant protein that is present in a sample (e.g., in serum) would be most valuable to remove. The identified, highly ionizable peptides can then be removed (e.g. by immunodepletion) from such a sample prior to MS analysis of a protein of interest.

In another embodiment of this method, the protein for which highly ionizing peptides are identified is found in a pathogen of interest or is produced by the pathogen. In this embodiment, a protein-containing sample from a subject that is suspected of being infected by the pathogen is treated to cleave proteins in the sample, and the resulting peptides are contacted with antibodies specific for the highly ionizable, pathogen-related, peptides. Highly ionizable peptides that are present in the sample are collected (concentrated, enriched), eluted, and subjected to MS. The presence of the highly ionizable peptides in the read-out (e.g., in a significantly increased amount compared to a baseline value, such as a comparable sample from a subject known not to be infected by the pathogen, or a suitable reference standard) indicates that the subject is infected with the pathogen. A similar analysis can be carried out to determine the presence of an organism, such as a pathogen, in a sample that is not from a subject (e.g., patient), such as an environmental sample.

In another embodiment of this method, the protein for which highly ionizing peptides are identified is a marker for a disease or disorder. In this embodiment, a sample from a subject suspected of having the disease or disorder is treated as above. The presence of the highly ionizable peptides in the MS read-out (e.g., in a significantly increased amount compared to a baseline value, such as a comparable sample from a subject known not to have the disease or disorder, or a suitable reference standard) indicates that the subject has or is likely to have the disease or disorder (is indicative of the presence of the disease or disorder); The predictive value of the individual peptides will vary according to the particular peptide and the disease or disorder, and should be able to be determined by those of skill in the art without undue experimentation.

Another aspect of the invention is a composition comprising one or more antibodies (e.g., polyclonal or monoclonal antibodies, active fragments of antibodies, such as Fab fragments, etc.) that are specific for one or more of the highly abundant and/or well-ionizing and/or proteotypic peptides of the invention. In one embodiment, the antibodies are attached (bound) to a surface, such as a bead, column material, pipette tip, etc. They may be arranged in an array, such as on a "chip." One aspect of the invention is a device comprising antibodies of the invention which are bound to a surface of the device. The device can be used, e.g., to pre-process samples for spectral analysis, or to collect and/or concentrate peptides to be analyzed by MS in a detection (e.g., diagnostic) assay.

Another aspect of the invention is a kit for performing one of the methods of the invention. The kit can comprise, e.g., a collection of antibodies that are specific for highly abundant and/or ionizable and/or proteotypic peptides and, optionally, packaging materials and/or instructions (e.g., written instructions) for use. The antibodies may be bound to a surface. A kit of the invention can be used, e.g., for pre-processing a sample for mass spectral analysis. In another embodiment, a kit of the invention can be used to isolate peptides, such as proteotypic peptides, e.g., for the detection of a protein of interest, such as a protein that is present in, or produced by, a pathogen, or a disease marker.

In one embodiment of the invention, proteins are identified whose presence in a sample is suspected of being detrimental during MS analysis of the sample. Representative peptides of those proteins are then identified for removal, e.g. by immunodepletion using antibodies that are specific for these peptides. The identification of these peptides as targets for antibody development is supported by conventional statistical analyses on the value of those targets and the predicted effect that their removal will have upon improvement in spectral quality. Upon identification of these peptide targets, antibodies for them are developed and purified, and solid-phase devices containing these antibodies are tested and validated for their ability to enhance the detection of lower abundance and other peptides in a complex mixture.

A method for identifying proteins (and peptides thereof) to be removed from a sample destined for MS analysis is illustrated herein for proteomics analysis of serum/plasma samples. Part I of the method—the identification of suitable protein targets for removal—is illustrated in the upper part of FIG. 1. Similar methods can be employed for samples from other tissue, organelle or cell sources, and for other types of analysis. Tables 5 and 2 shows representative lists of suitable protein (Table 5) and peptide (Table 2) targets for serum/plasma samples. These proteins have been identified through literature searches of the most abundant proteins in serum (Anderson et al. (2002) *Proteomics* 1, 845-867), and for commonly observed contaminant peaks (Ding et al. (2003)) in, e.g., MALDI and ESI MS. It is noted that multiple types or isoforms of keratin are included, as they are commonly observed in MS data.

Part II of the method—the identification of suitable peptides of the proteins identified in Part I of the method—is illustrated in the bottom portion of FIG. 1. Selected protein targets are cleaved by an enzymatic or chemical method. In this illustration, trypsin is used to digest the proteins. However, as discussed elsewhere herein, a variety of other enzymes or chemical methods can also be used. In this step, peptides are identified which, when removed from the peptide mixture, allow for the most beneficial improvement in the spectra, thereby resulting in enhanced detection of other peptides. Data from previously published reports, PRIDE database [EBI], and any database archiving peptide/protein data that includes peptide ionization potentials, can be employed, and can be combined with the number of observations of the peptides counted by the investigator, to create a database of potential peptide targets. The identification of peptide targets is initiated by pooling data obtained from both in vitro tryptic digestions of purified proteins, and the mining of database search results. The potential peptide target database preferably contains peptides that are amenable to antibody development (e.g. consisting of about 5-20, or more, amino acids, e.g., about 8-15 amino acids in length). Generally, an alignment search (e.g. a BLAST search) is performed to ensure that each peptide is specific to the protein, or class of proteins (e.g. all keratins, all immunoglobulins, etc.) that is targeted for removal. Following these filters, conventional bioinformatics and statistical analyses are employed to further define the peptide targets, to ensure specificity and maximum potential for spectral enhancement, etc. Such analyses include, e.g., assessment of the most commonly observed peptides, probability of observation, probability that the peptide will be observed at maximum (or near maximum) relative intensity, and probability that the peptide interferes with the ability to detect other peptides. In general, for each target protein, about 2-8 (e.g., about 3-5) peptides are identified that fit these criteria and are selected for further processing in Part III of the method.

Part III of the method (illustrated in the top portion of FIG. 2) comprises the development and purification (e.g. affinity purification) of antibodies (e.g., polyclonal antisera and/or monoclonal antibodies) that are specific for the selected target peptides. These antibodies are then coupled to a solid phase, such as a matrix, bead or other column material, which can then be used in spin-column, chromatography column, pipette tip, or other device format.

Figure 2:
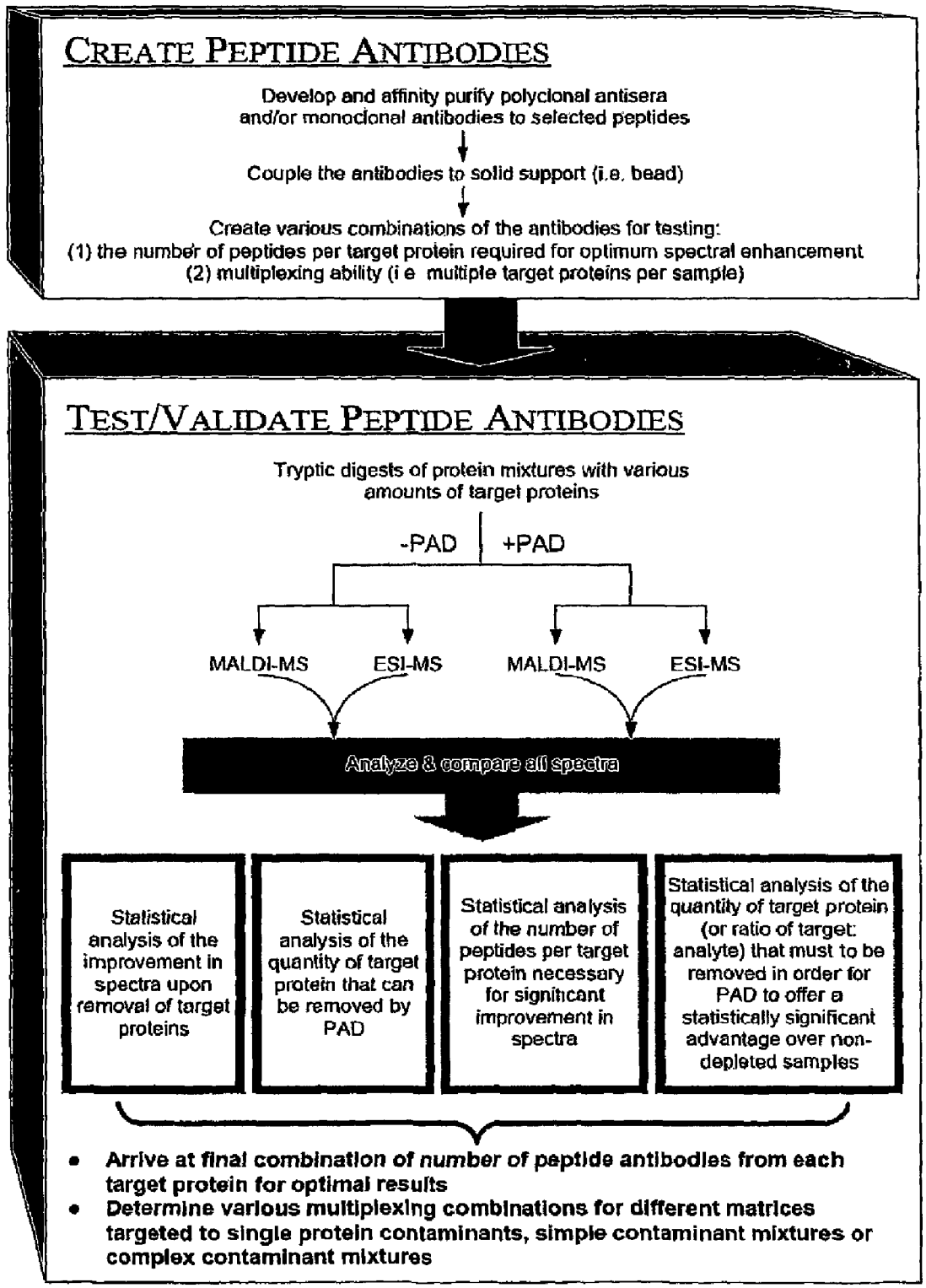
FIG. 2 shows diagrammatically Part III of the PAD development workflow.

Part IV of the method (PAD development workflow) is shown in the bottom portion of FIG. 2: the peptide antibodies and resulting device(s) are validated, using a number of different peptide mixtures. For both MALDI and ESI MS, the number and combination of peptide antibodies required for a statistically significant improvement in spectra and detection of low abundance and other peptides is evaluated. This evaluation includes a determination of the amount of high abundance/contaminant peptides that can be removed by PAD, the number of peptides per protein required for desired enhancement of spectra, and the amount of target peptides (or ratio of target to analyte) that must be removed for desired enhancement of spectra. In embodiments of the invention, a device so defined contains one or more (e.g. a mixture of) antibodies to peptides, so that multiple target peptides from multiple proteins can be removed with a single device. In other embodiments, the device contains one or more (e.g. multiple) antibodies to peptides for the removal of peptides from a single protein target.

Example I describes a procedure in which immunodepletion of samples with antibodies against keratins was shown to improve spectral quality during mass spectrometry of the samples.

Example II describes a procedure in which immunodepletion of about 25 peptides (about 1-5 peptides from each of about eight proteins) is shown to improve spectral quality during mass spectrometry of the samples.

A number of highly abundant proteins (sometimes referred to herein as "high abundant" or "high abundance" proteins) and/or common contaminating proteins, or peptides of those proteins, have been identified that are desirably removed from samples destined for mass spectrometry (sometimes referred to here in as mass spectroscopy or mass spectral analysis).

Among such high abundance proteins are the 14 serum/plasma proteins which have been targeted for removal by commercially available columns. These are listed in Table 5.

TABLE 5

Highly abundant serum/plasma proteins removed by the MARS (Agilent Technologies) and ProteomeLab IgY 12 (Beckman-Coulter) immunoaffinity columns.

| Protein | Removed by MARS | Removed by IgY 12 |
| --- | --- | --- |
| Albumin | X | X |
| Alpha-1-acid glycoprotein | X | X |
| Alpha-1-antitrypsin | X | X |
| Alpha-2-macroglobulin | X | X |
| Apolipoprotein AI | X | X |
| Apolipoprotein AII | X | X |
| Complement C3 | X | |
| Fibrinogen | X | X |
| Haptoglobin | X | X |
| IgA | X | X |
| IgG | X | X |
| IgM | X | X |

TABLE 5-continued

Highly abundant serum/plasma proteins removed by the MARS (Agilent Technologies) and ProteomeLab IgY 12 (Beckman-Coulter) immunoaffinity columns.

| Protein | Removed by MARS | Removed by IgY 12 |
| --- | --- | --- |
| Transferrin | X | X |
| Transthyretin | X | |

As indicated in the Table, 12 of these high abundance serum proteins are targeted by the commercially available column manufactured by Beckman-Coulter (ProteomeLab™ IgY-12), and all 14 of them by the column manufactured by Agilent (MARS column). Other abundant tissue or subproteome proteins whose removal can be beneficial for MS analysis include, e.g., actin isoforms, tropomyosin, and other cytoskeletal proteins, collagen and glycolytic proteins. Other potentially contaminating proteins include enzymes (e.g., proteases, such as trypsin or chymotrypsin) that have been used to digest the proteins in a sample to peptides.

In addition to these high abundance protein targets, several previously published studies on the observation of common contaminant peptide masses in PMF (peptide mass fingerprinting) data provide a useful database of common contaminant masses. For example, a report by Ding et al. (2003) *Proteomics* 3, 1313-1317 examined 3764 masses from 118 experimental PMF spectra and sorted out the 100 most frequently occurring contaminant masses. Table 2 lists 42 of these peptides, which are the most commonly observed peptides from keratins and typsin using MALDI-MS (as opposed to ESI-MS as used in Table 4).

TABLE 2

Interference probability, protein source, and peptide sequence of 42 commonly observed contaminant masses in MALDI as compiled by Ding, et al. (2003, supra)

| Interference probability | Protein | Peptide Sequence |
| --- | --- | --- |
| 85 | Trypsin | LGEHNIDVLEGNEQFINAAK (SEQ ID NO: 1) |
| 73 | Trypsin | IITHPNFNGNTLDNDIMLIK (SEQ ID NO: 2) |
| 64 | Trypsin | VATVSLPR (SEQ ID NO: 3) |
| 56 | Keratin 9 | GGGGSFGYSYGGGSGGGFSA SSLGGGFGGGSR (SEQ ID NO: 4) |
| 47 | Keratin 10 | NVSTGDVNVEMNAAPGVDLT QLLNNMR (SEQ ID NO: 5) |
| 43 | Keratin 10 | GSLGGGFSSGGFSGGSFSR (SEQ ID NO: 6) |
| 43 | Keratin 1 | LALDLEIATYR (SEQ ID NO: 7) |
| 42 | Keratin 1 | THNLEPYFESFINNLR (SEQ ID NO: 8) |
| 40 | Keratin 1 | YEELQITAGR (SEQ ID NO: 9) |
| 37 | Keratin 9 | MSCRQFSSSYLSRSGGGGGG GLGSGGSIR (SEQ ID NO: 10) |
| 36 | Keratin 1 | WELLQQVDTSTR (SEQ ID NO: 11) |
| 30 | Keratin 1 | GSYGSGGSSYGSGGGSYGSGGGGGHGSYGSGSSSGGYR (SEQ ID NO: 12) |
| 29 | Keratin 10 | NQILNLTTDNANILLQIDNA R (SEQ ID NO: 13) |
| 29 | Keratin 10 | SGGGGGGGGCGGGGGVSSLR (SEQ ID NO: 14) |

TABLE 2-continued

Interference probability, protein source, and peptide sequence of 42 commonly observed contaminant masses in MALDI as compiled by Ding, et al. (2003, supra)

| Interference probability | Protein | Peptide Sequence |
|---|---|---|
| 24 | Keratin 9 | FEMEQNLR (SEQ ID NO: 15) |
| 20 | Keratin 1 | NMQDMVEDYR (SEQ ID NO: 16) |
| 20 | Keratin 10 | SQYEQLAEQNR (SEQ ID NO: 17) |
| 19 | Keratin 1 | IEISELNR (SEQ ID NO: 18) |
| 19 | Keratin 1 | QISNLQQSISDAEQR (SEQ ID NO: 19) |
| 19 | Keratin 9 | SDLEMQYETLQEELMALKK (SEQ ID NO: 20) |
| 16 | Keratin 10 | LENEIOTYR (SEQ ID NO: 21) |
| 15 | Keratin 9 | GGSGGSYGGGGSGGGYGGGS GSR (SEQ ID NO: 22) |
| 12 | Keratin 1 | GGGGGGYGSGGSSYGSGGGSYGSGGGGGGR (SEQ ID NO: 23) |
| 12 | Keratin 1 | SGGGFSSGSAGIINYQR (SEQ ID NO: 24) |
| 10 | Trypsin | NKPGVYTK (SEQ ID NO: 25) |
| 10 | Keratin 1 | SLNNQFASFIDK (SEQ ID NO: 26) |
| 9 | Keratin 10 | AETECQNTEYQQLLDIK (SEQ ID NO: 27) |
| 9 | Keratin 10 | VTMQNLNDR (SEQ ID NO: 28) |
| 8 | Keratin 10 | HGNSHQGEPR (SEQ ID NO: 29) |
| 8 | Keratin 9 | HGVQELEIELQSQLSK (SEQ ID NO: 30) |
| 8 | Keratin 10 | NVQALEIELQSQLALK (SEQ ID NO: 31) |
| 8 | Keratin 10 | SLLEGEGSSGGGR (SEQ ID NO: 32) |
| 6 | Keratin 9 | QEIECQNQEYSLLLSIK (SEQ ID NO: 33) |
| 4 | Keratin 1 | FSSCGGGGGSFGAGGGFGSR (SEQ ID NO: 34) |
| 4 | Keratin 9 | NYSPYYNTIDDLK (SEQ ID NO: 35) |
| 4 | Keratin 1 | SEIDNVK (SEQ ID NO: 36) |
| 4 | Keratin 1 | SISISVAR (SEQ ID NO: 37) |
| 4 | Keratin 1 | TLLEGEESR (SEQ ID NO: 38) |
| 3 | Keratin 9 | GPAAIQK (SEQ ID NO: 39) |
| 3 | Keratin 10 | LAADDFR (SEQ ID NO: 40) |
| 3 | Keratin 1 | MSGECAPNVSVSVSTSHTTI SGGGSR (SEQ ID NO: 41) |
| 3 | Keratin 9 | MTLDDFR (SEQ ID NO: 42) |

As can be seen from this Table, trypsin and several keratins are the source of the most commonly observed contaminant masses from these spectra. Consistent with the observation of Ding et al. (2003, supra), Schmidt et al. (2003) *J Am Soc Mass Spectrum* 14, 943-956 also reports that peptides from keratins and trypsin were observed in >5% of 480 PMF spectra. Furthermore, a similar report by Parker et al. (1998) *Electrophoresis* 19, 1920-1032 also lists keratins and trypsin as common contaminant peaks. See also Zolotarjova et al. (2005) *Proteomics* 5, 3304-3313, for a review of the proteins targeted for removal by commercially available methods.

Potentially contaminating peptides of some of the most abundant proteins in human serum/plasma are listed in Table 3. This table lists the predicted peptides following an in silico tryptic digest of 11 of the 14 most abundant proteins in human serum/plasma (listed in table 5). This table is not meant to be all inclusive of all of the potential peptides that could be observed, as sometimes trypsin may miss a site and thus lead to 'missed cleaveage'. Thus, this table provides an example of the types of data one would expect to observe after a tryptic digest of these proteins in serum/plasma. The list of proteins is independent of the type of mass spectrometer that is being used to acquire the data.

TABLE 3

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 2917.32 | SHCIAEVENDEMPADLPSLA ADFVESK | Albumin |
| 2593.24 | LVRPEVDVMCTAFHDNEETF LK | Albumin |
| 2433.26 | ALVLIAFAQYLQQCPFEDHV K | Albumin |
| 2404.17 | MPCAEDYLSVVLNQLCVLHE K | Albumin |
| 2203.00 | EFNAETFTFHADICTLSEK | Albumin |
| 2045.10 | VFDEFKPLVEEPQNLIK | Albumin |
| 1915.77 | VHTECCHGDLLECADDR | Albumin |
| 1853.91 | RPCFSALEVDETYVPK | Albumin |
| 1742.89 | HPYFYAPELLFFAK | Albumin |
| 1623.79 | DVFLGMFLYEYAR | Albumin |
| 1600.73 | QNCELFEQLGEYK | Albumin |
| 1511.84 | VPQVSTPTLVEVSR | Albumin |
| 1386.62 | YICENQDSISSK | Albumin |
| 1384.54 | TCVADESAENCDK | Albumin |
| 1381.53 | CCAAADPHECYAK | Albumin |
| 1342.63 | AVMDDFAAFVEK | Albumin |
| 1320.49 | ETYGEMADCCAK | Albumin |
| 1311.74 | HPDYSVVLLLR | Albumin |
| 1257.52 | AAFTECCQAADK | Albumin |
| 1191.57 | ECCEKPLLEK | Albumin |
| 1149.62 | LVNEVTEFAK | Albumin |
| 1024.46 | CCTESLVNR | Albumin |
| 1018.48 | NECFLQHK | Albumin |
| 1017.54 | SLHTLFGDK | Albumin |
| 1013.60 | LVAASQAALGL | Albumin |
| 1013.42 | ETCFAEEGK | Albumin |
| 1000.60 | QTALVELVK | Albumin |
| 984.49 | TYETTLEK | Albumin |
| 960.56 | FQNALLVR | Albumin |
| 951.44 | DLGEENFK | Albumin |
| 940.45 | DDNPNLPR | Albumin |
| 927.49 | YLYEIAR | Albumin |
| 880.44 | AEFAEVSK | Albumin |
| 876.50 | LCTVATLR | Albumin |
| 789.47 | LVTDLTK | Albumin |
| 715.42 | AACLLPK | Albumin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 698.36 | SEVAHR | Albumin |
| 695.34 | NYAEAK | Albumin |
| 674.35 | TPVSDR | Albumin |
| 673.38 | AWAVAR | Albumin |
| 658.32 | QEPER | Albumin |
| 2519.39 | QIPLCANLVPVPITNATLDQ ITGK | Alpha-1-acid glycoprotein |
| 1919.95 | SVQEIQATFFYFTPNK | Alpha-1-acid glycoprotein |
| 1858.88 | QDQCIYNTTYLNVQR | Alpha-1-acid glycoprotein |
| 1752.95 | YVGGQEHFAHLLILR | Alpha-1-acid glycoprotein |
| 1708.85 | NWGLSVYADKPETTK | Alpha-1-acid glycoprotein |
| 1685.78 | EQLGEFYEALDCLR | Alpha-1-acid glycoprotein |
| 1445.66 | TYMLAFDVNDEK | Alpha-1-acid glycoprotein |
| 1160.59 | WFYIASAFR | Alpha-1-acid glycoprotein |
| 1112.53 | SDVVYTDWK | Alpha-1-acid glycoprotein |
| 994.52 | TEDTIFLR | Alpha-1-acid glycoprotein |
| 796.35 | NEEYNK | Alpha-1-acid glycoprotein |
| 776.39 | ENGTISR | Alpha-1-acid glycoprotein |
| 718.34 | CEPLEK | Alpha-1-acid glycoprotein |
| 696.33 | EYQTR | Alpha-1-acid glycoprotein |
| 678.26 | QEEGES | Alpha-1-acid glycoprotein |
| 3691.82 | ADTHDEILEGLNFNLTEIPE AQIHEGFQELLR | Alpha-1-antitrypsin |
| 3181.64 | QLAHQSNSTNIFFSPVSIAT AFAMLSLGTK | Alpha-1-antitrypsin |
| 2574.34 | TLNQPDSQLQLTTGNGLFLS EGLK | Alpha-1-antitrypsin |
| 2259.14 | GTEAAGAMFLEAIPMSIPPE VK | Alpha-1-antitrypsin |
| 2057.95 | LYHSEAFTVNFGDTEEAK | Alpha-1-antitrypsin |
| 1891.86 | DTEEEDFHVDQVTTVK | Alpha-1-antitrypsin |
| 1855.98 | FNKPFVFLMIEQNTK | Alpha-1-antitrypsin |
| 1833.92 | VFSNGADLSGVTEEAPLK | Alpha-1-antitrypsin |
| 1803.96 | LQHLENELTHDIITK | Alpha-1-antitrypsin |
| 1779.77 | TDTSHHDQDHPTFNK | Alpha-1-antitrypsin |
| 1755.90 | YLGNATAIFFLPDEGK | Alpha-1-antitrypsin |
| 1641.86 | ITPNLAEFAFSLYR | Alpha-1-antitrypsin |
| 1576.84 | DTVFALVNYIFFK | Alpha-1-antitrypsin |
| 1190.58 | LGMFNIQHCK | Alpha-1-antitrypsin |
| 1110.60 | LSITGTYDLK | Alpha-1-antitrypsin |
| 1090.57 | WERPFEVK | Alpha-1-antitrypsin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1076.62 | LSSWVLLMK | Alpha-1-antitrypsin |
| 1058.47 | EDPQGDAAQK | Alpha-1-antitrypsin |
| 1015.61 | SVLGQLGITK | Alpha-1-antitrypsin |
| 1008.50 | QINDYVEK | Alpha-1-antitrypsin |
| 922.43 | FLENEDR | Alpha-1-antitrypsin |
| 888.50 | AVLTIDEK | Alpha-1-antitrypsin |
| 852.49 | SASLHLPK | Alpha-1-antitrypsin |
| 785.45 | VVNPTQK | Alpha-1-antitrypsin |
| 779.41 | SPLFMGK | Alpha-1-antitrypsin |
| 750.40 | FLEDVK | Alpha-1-antitrypsin |
| 686.44 | IVDLVK | Alpha-1-antitrypsin |
| 3827.94 | SFVHLEPMSHELPCGHTQTV QAHYILNGGTLLGLK | Alpha-2-macroglobulin |
| 3804.78 | GNEANYYSNATTDEHGLVQF SINTTNVMGTSLTVR | Alpha-2-macroglobulin |
| 3720.88 | YFPETWIWDLVVVNSAGVAE VGVTVPDTITEWK | Alpha-2-macroglobulin |
| 3620.85 | IITILEEEMNVSVCGLYTYG KPVPGHVTVSICR | Alpha-2-macroglobulin |
| 3356.61 | SLGNVNFTVSAEALESQELC GTEVPSVPEHGR | Alpha-2-macroglobulin |
| 3281.46 | SPCYGYQWVSEEHEEAHHTA YLVFSPSK | Alpha-2-macroglobulin |
| 3205.77 | GGVEDEVTLSAYITIALLEI PLTVTHPVVR | Alpha-2-macroglobulin |
| 2917.52 | AVDQSVLLMKPDAELSASSV YNLLPEK | Alpha-2-macroglobulin |
| 2810.44 | VVSMDENFHPLNELIPLVYI QDPK | Alpha-2-macroglobulin |
| 2544.34 | SVSGKPQYMVLVPSLLHTET TEK | Alpha-2-macroglobulin |
| 2491.06 | VYDYYETDEFAIAEYNAPCS K | Alpha-2-macroglobulin |
| 2418.20 | SLFTDLEAENDVLHCVAFAV PK | Alpha-2-macroglobulin |
| 2388.27 | AYIFIDEAHITQALIWLSQR | Alpha-2-macroglobulin |
| 2387.19 | QQNAQGGFSSTQDTVVALHA LSK | Alpha-2-macroglobulin |
| 2340.21 | GCVLLSYLNETVTVSASLES VR | Alpha-2-macroglobulin |
| 2340.13 | ETTFNSLLCPSGGEVSEELS LK | Alpha-2-macroglobulin |
| 2249.08 | EEFPFALGVQTLPQTCDEPK | Alpha-2-macroglobulin |
| 2233.97 | DLTGFPGPLNDQDDEDCINR | Alpha-2-macroglobulin |
| 2163.18 | VSNQTLSLFFTVLQDVPVR | Alpha-2-macroglobulin |
| 2137.06 | HNVYINGITYTPVSSTNEK | Alpha-2-macroglobulin |
| 2110.08 | LHTEAQIQEEGTVVELTGR | Alpha-2-macroglobulin |
| 2049.05 | VDLSFSPSQSLPASHAHLR | Alpha-2-macroglobulin |
| 2045.10 | LLLQQVSLPELPGEYSMK | Alpha-2-macroglobulin |
| 2045.06 | AFQPFFVELTMPYSVIR | Alpha-2-macroglobulin |
| 2025.99 | AGAFCLSEDAGLGISSTASL R | Alpha-2-macroglobulin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 2016.91 | MCPQLQQYEMHGPEGLR | Alpha-2-macroglobulin |
| 1991.74 | YSDASDCHGEDSQAFCEK | Alpha-2-macroglobulin |
| 1884.05 | VSVQLEASPAFLAVPVEK | Alpha-2-macroglobulin |
| 1848.88 | QFSFPLSSEPFQGSYK | Alpha-2-macroglobulin |
| 1845.04 | LLIYAVLPTGDVIGDSAK | Alpha-2-macroglobulin |
| 1842.86 | FSGQLNSHGCFYQQVK | Alpha-2-macroglobulin |
| 1840.92 | AHTSFQISLSVSYTGSR | Alpha-2-macroglobulin |
| 1780.01 | DTVIKPLLVEPEGLEK | Alpha-2-macroglobulin |
| 1697.84 | SSSNEEVMFLTVQVK | Alpha-2-macroglobulin |
| 1672.86 | TEHPFTVEEFVLPK | Alpha-2-macroglobulin |
| 1620.82 | DNSVHWERPQKPK | Alpha-2-macroglobulin |
| 1617.85 | TEVSSNHVLIYLDK | Alpha-2-macroglobulin |
| 1604.84 | IAQWQSFQLEGGLK | Alpha-2-macroglobulin |
| 1565.83 | ALLAYAFALAGNQDK | Alpha-2-macroglobulin |
| 1545.80 | LVHVEEPHTETVR | Alpha-2-macroglobulin |
| 1529.70 | TAQEGDHGSHVYTK | Alpha-2-macroglobulin |
| 1511.77 | AAQVTIQSSGTFSSK | Alpha-2-macroglobulin |
| 1497.76 | VTGEGCVYLQTSLK | Alpha-2-macroglobulin |
| 1491.80 | NQGNTWLTAFVLK | Alpha-2-macroglobulin |
| 1448.64 | DMYSFLEDMGLK | Alpha-2-macroglobulin |
| 1418.60 | HYDGSYSTFGER | Alpha-2-macroglobulin |
| 1416.83 | MVSGFIPLKPTVK | Alpha-2-macroglobulin |
| 1394.68 | NEDSLVFVQTDK | Alpha-2-macroglobulin |
| 1298.57 | EQAPHCICANGR | Alpha-2-macroglobulin |
| 1281.63 | NALFCLESAWK | Alpha-2-macroglobulin |
| 1259.57 | VGFYESDVMGR | Alpha-2-macroglobulin |
| 1255.64 | AIGYLNTGYQR | Alpha-2-macroglobulin |
| 1248.67 | LSFYYLIMAK | Alpha-2-macroglobulin |
| 1215.65 | VTAAPQSVCALR | Alpha-2-macroglobulin |
| 1210.64 | LPPNVVEESAR | Alpha-2-macroglobulin |
| 1168.53 | YDVENCLANK | Alpha-2-macroglobulin |
| 1148.62 | QGIPFFGQVR | Alpha-2-macroglobulin |
| 1134.58 | SASNMAIVDVK | Alpha-2-macroglobulin |
| 1120.64 | SIYKPGQTVK | Alpha-2-macroglobulin |
| 1116.60 | QTVSWAVTPK | Alpha-2-macroglobulin |
| 1103.61 | SSGSLLNNAIK | Alpha-2-macroglobulin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
| --- | --- | --- |
| 1084.61 | GHFSISIPVK | Alpha-2-macroglobulin |
| 1046.59 | FEVQVTVPK | Alpha-2-macroglobulin |
| 1018.59 | ATVLNYLPK | Alpha-2-macroglobulin |
| 1006.47 | FQVDNNNR | Alpha-2-macroglobulin |
| 925.55 | TGTHGLLVK | Alpha-2-macroglobulin |
| 889.46 | SLNEEAVK | Alpha-2-macroglobulin |
| 886.44 | YGAATFTR | Alpha-2-macroglobulin |
| 883.56 | DLKPAIVK | Alpha-2-macroglobulin |
| 876.48 | YNILPEK | Alpha-2-macroglobulin |
| 828.46 | SDIAPVAR | Alpha-2-macroglobulin |
| 820.42 | QSSEITR | Alpha-2-macroglobulin |
| 806.40 | GPTQEFK | Alpha-2-macroglobulin |
| 765.41 | GEAFTLK | Alpha-2-macroglobulin |
| 760.37 | VDSHFR | Alpha-2-macroglobulin |
| 724.44 | GVPIPNK | Alpha-2-macroglobulin |
| 711.29 | DNGCFR | Alpha-2-macroglobulin |
| 699.35 | SNHVSR | Alpha-2-macroglobulin |
| 699.30 | EYEMK | Alpha-2-macroglobulin |
| 693.37 | TFAQAR | Alpha-2-macroglobulin |
| 678.39 | TTVMVK | Alpha-2-macroglobulin |
| 667.34 | AFTNSK | Alpha-2-macroglobulin |
| 665.36 | QLNYK | Alpha-2-macroglobulin |
| 650.28 | QEDMK | Alpha-2-macroglobulin |
| 1932.93 | EQLGPVTQEFWDNLEK | Apolipoprotein AI |
| 1612.79 | LLDNWDSVTSTFSK | Apolipoprotein AI |
| 1400.67 | DYVSQFEGSALGK | Apolipoprotein AI |
| 1386.72 | VSFLSALEEYTK | Apolipoprotein AI |
| 1301.65 | THLAPYSDELR | Apolipoprotein AI |
| 1283.57 | WQEEMELYR | Apolipoprotein AI |
| 1252.62 | VQPYLDDFQK | Apolipoprotein AI |
| 1235.69 | DLATVYVDVLK | Apolipoprotein AI |
| 1230.71 | QGLLPVLESFK | Apolipoprotein AI |
| 1226.54 | DEPPQSPWDR | Apolipoprotein AI |
| 1215.62 | ATEHLSTLSEK | Apolipoprotein AI |
| 1031.52 | LSPLGEEMR | Apolipoprotein AI |
| 1012.58 | AKPALEDLR | Apolipoprotein AI |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 896.48 | LHELQEK | Apolipoprotein AI |
| 873.44 | AELQEGAR | Apolipoprotein AI |
| 831.44 | LAEYHAK | Apolipoprotein AI |
| 781.43 | AHVDALR | Apolipoprotein AI |
| 732.38 | DLEEVK | Apolipoprotein AI |
| 704.36 | ETEGLR | Apolipoprotein AI |
| 2385.20 | AGTELVNFLSYFVELGTQPA TQ | Apolipoprotein AII |
| 2293.07 | EPCVESLVSQYFQTVTDYGK | Apolipoprotein AII |
| 972.50 | SPELQAEAK | Apolipoprotein AII |
| 941.57 | EQLTPLIK | Apolipoprotein AII |
| 673.32 | SYFEK | Apolipoprotein AII |
| 3926.88 | HLIVTPSGCGEQNMIGMTPT VIAVHYLDETEQWEK | Complement C3 |
| 3282.65 | QDSLSSQNQLGVLPLSWDIP ELVNMGQWK | Complement C3 |
| 3250.56 | LESEETMVLEAHDAQGDVPV TVTVHDFPGK | Complement C3 |
| 2841.41 | HYLMWGLSSDFWGEKPNLSY IIGK | Complement C3 |
| 2788.24 | GDQDATMSILDISMMTGFAP DTDDLK | Complement C3 |
| 2749.32 | YFKPGMPFDLMVFVTNPDGS PAYR | Complement C3 |
| 2679.25 | YYGGGYGSTQATFMVFQALA QYQK | Complement C3 |
| 2578.31 | TMQALPYSTVGNSNNYLHLS VLR | Complement C3 |
| 2564.29 | QKPDGVFQEDAPVIHQEMIG GLR | Complement C3 |
| 2546.00 | DTWVEHWPEEDECQDEENQK | Complement C3 |
| 2494.15 | DYAGVFSDAGLTFTSSSGQQ TAQR | Complement C3 |
| 2444.31 | EPGQDLVVLPLSITTDFIPS FR | Complement C3 |
| 2415.17 | GICVADPFEVTVMQDFFIDL R | Complement C3 |
| 2263.14 | SLYVSATVILHSGSDMVQAE R | Complement C3 |
| 2257.11 | VQLSNDFDEYIMAIEQTIK | Complement C3 |
| 2255.16 | TVLTPATNHMGNVTFTIPAN R | Complement C3 |
| 2214.00 | EDIPPADLSDQVPDTESETR | Complement C3 |
| 2198.13 | VPVAVQGEDTVQSLTQGDGV AK | Complement C3 |
| 2166.00 | AYYENSPQQVFSTEFEVK | Complement C3 |
| 2160.21 | VFSLAVNLIAIDSQVLCGAV K | Complement C3 |
| 2157.09 | ILLQGTPVAQMTEDAVDAER | Complement C3 |
| 2151.21 | QLYNVEATSYALLALLQLK | Complement C3 |
| 2147.07 | DAPDHQELNLDVSLQLPSR | Complement C3 |
| 2045.88 | QCQDLGAFTESMVVFGCPN | Complement C3 |
| 1910.06 | VVLVSLQSGYLFIQTDK | Complement C3 |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
| --- | --- | --- |
| 1891.08 | LSINTHPSQKPLSITVR | Complement C3 |
| 1878.97 | EYVLPSFEVIVEPTEK | Complement C3 |
| 1878.89 | SEFPESWLWNVEDLK | Complement C3 |
| 1872.03 | TELRPGETLNVNFLLR | Complement C3 |
| 1865.94 | VEGTAFVIFGIQDGEQR | Complement C3 |
| 1841.99 | VHQYFNVELIQPGAVK | Complement C3 |
| 1816.89 | SNLDEDIIAEENIVSR | Complement C3 |
| 1795.88 | DSITTWEILAVSMSDK | Complement C3 |
| 1787.97 | SGIPIVTSPYQIHFTK | Complement C3 |
| 1749.95 | DMALTAFVLISLQEAK | Complement C3 |
| 1743.91 | VELLHNPAFCSLATTK | Complement C3 |
| 1732.84 | DICEEQVNSLPGSITK | Complement C3 |
| 1671.85 | SYTVAIAGYALAQMGR | Complement C3 |
| 1653.88 | FVTVQATFGTQVVEK | Complement C3 |
| 1641.77 | AGDFLEANYMNLQR | Complement C3 |
| 1639.87 | TVMVNIENPEGIPVK | Complement C3 |
| 1610.72 | VYAYYNLEESCTR | Complement C3 |
| 1588.75 | VFLDCCNYITELR | Complement C3 |
| 1511.82 | LVAYYTLIGASGQR | Complement C3 |
| 1504.82 | SPMYSIITPNILR | Complement C3 |
| 1491.76 | GQGTLSVVTMYHAK | Complement C3 |
| 1471.74 | AAVYHHFISDGVR | Complement C3 |
| 1470.78 | IPIEDGSGEVVLSR | Complement C3 |
| 1401.84 | SSLSVPYVIVPLK | Complement C3 |
| 1370.73 | TIYTPGSTVLYR | Complement C3 |
| 1350.60 | VSHSEDDCLAFK | Complement C3 |
| 1345.70 | EVVADSVWVDVK | Complement C3 |
| 1335.73 | APSTWLTAYVVK | Complement C3 |
| 1289.61 | SGSDEVQVGQQR | Complement C3 |
| 1281.60 | ENEGFTVTAEGK | Complement C3 |
| 1261.60 | QELSEAEQATR | Complement C3 |
| 1243.57 | ACEPGVDYVYK | Complement C3 |
| 1226.66 | QPVPGQQMTLK | Complement C3 |
| 1212.68 | VTIKPAPETEK | Complement C3 |
| 1211.65 | IHWESASLLR | Complement C3 |
| 1208.60 | YYTYLIMNK | Complement C3 |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1193.60 | NTMILEICTR | Complement C3 |
| 1190.62 | DFDFVPPVVR | Complement C3 |
| 1184.51 | CAEENCFIQK | Complement C3 |
| 1183.59 | AELQCPQPAAR | Complement C3 |
| 1152.60 | QPSSAFAAFVK | Complement C3 |
| 1148.64 | HQQTVTIPPK | Complement C3 |
| 1139.54 | FYYIYNEK | Complement C3 |
| 1110.63 | VLLDGVQNPR | Complement C3 |
| 1092.63 | NTLIIYLDK | Complement C3 |
| 1083.56 | GYTQQLAFR | Complement C3 |
| 1006.52 | DSCVGSLVVK | Complement C3 |
| 1005.47 | ADIGCTPGSGK | Complement C3 |
| 1002.55 | TGLQEVEVK | Complement C3 |
| 967.49 | FISLGEACK | Complement C3 |
| 959.55 | GLEVTITAR | Complement C3 |
| 898.48 | AVLYNYR | Complement C3 |
| 888.48 | IWDVVEK | Complement C3 |
| 887.46 | NEQVEIR | Complement C3 |
| 886.52 | ISLPESLK | Complement C3 |
| 878.52 | LMNIFLK | Complement C3 |
| 872.46 | QLANGVDR | Complement C3 |
| 871.52 | QGALELIK | Complement C3 |
| 858.48 | IFTVNHK | Complement C3 |
| 854.41 | IEGDHGAR | Complement C3 |
| 845.43 | WLNEQR | Complement C3 |
| 842.53 | VVLVAVDK | Complement C3 |
| 833.49 | LPYSVVR | Complement C3 |
| 824.47 | ASHLGLAR | Complement C3 |
| 821.38 | DQLTCNK | Complement C3 |
| 820.40 | FYHPEK | Complement C3 |
| 813.27 | CCEDGMR | Complement C3 |
| 805.48 | TFISPIK | Complement C3 |
| 804.45 | SVQLTEK | Complement C3 |
| 801.49 | WLILEK | Complement C3 |
| 778.33 | SGQSEDR | Complement C3 |
| 776.47 | GVFVLNK | Complement C3 |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 775.46 | LVLSSEK | Complement C3 |
| 769.46 | VVPEGIR | Complement C3 |
| 759.40 | QNQELK | Complement C3 |
| 746.40 | VTLEER | Complement C3 |
| 731.39 | AEDLVGK | Complement C3 |
| 731.34 | WEDPGK | Complement C3 |
| 730.37 | TLDPER | Complement C3 |
| 714.39 | RPQDAK | Complement C3 |
| 680.40 | FLTTAK | Complement C3 |
| 667.33 | YELDK | Complement C3 |
| 654.43 | LLPVGR | Complement C3 |
| 3071.38 | EVVTSEDGSDCPEAMDLGTL SGIGTLDGFR | Fibrinogen |
| 2967.39 | GFGSLNDEGEGEFWLGNDYL HLLTQR | Fibrinogen |
| 2456.23 | IFSVYCDQETSLGGWLLIQQ R | Fibrinogen |
| 2275.07 | DCDDVLQTHPSGTQSGIFNI K | Fibrinogen |
| 2265.05 | TFPGFFSPMLGEFVSETESR | Fibrinogen |
| 2198.98 | VELEDWAGNEAYAEYHFR | Fibrinogen |
| 2009.97 | NNSPYEIENGVVWVSFR | Fibrinogen |
| 1963.85 | NPSSAGSWNSGSSGPGSTGN R | Fibrinogen |
| 1906.72 | DSDWPFCSDEDWNYK | Fibrinogen |
| 1872.77 | MADEAGSEADHEGTHSTK | Fibrinogen |
| 1637.77 | ESSSHHPGIAEFPSR | Fibrinogen |
| 1629.83 | DSHSLTTNIMEILR | Fibrinogen |
| 1593.72 | HPDEAAFFDTASTGK | Fibrinogen |
| 1572.68 | GGSTSYGTGSETESPR | Fibrinogen |
| 1520.73 | GLIDEVNQDFTNR | Fibrinogen |
| 1501.74 | MELERPGGNEITR | Fibrinogen |
| 1441.79 | MKPVPDLVPGNFK | Fibrinogen |
| 1190.54 | QFTSSTSYNR | Fibrinogen |
| 1140.55 | GSESGIFTNTK | Fibrinogen |
| 1106.67 | VQHIQLLQK | Fibrinogen |
| 1062.51 | ALTDMPQMR | Fibrinogen |
| 1053.48 | MDGSLNFNR | Fibrinogen |
| 1028.50 | NSLFEYQK | Fibrinogen |
| 1010.51 | VTSGSTTTR | Fibrinogen |
| 967.42 | GDFSSANNR | Fibrinogen |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 944.53 | LEVDIDIK | Fibrinogen |
| 928.55 | QLEQVIAK | Fibrinogen |
| 925.39 | DYEDQQK | Fibrinogen |
| 923.49 | TVIGPDGHK | Fibrinogen |
| 870.38 | GDSTFESK | Fibrinogen |
| 848.54 | QHLPLIK | Fibrinogen |
| 840.39 | TWQDYK | Fibrinogen |
| 826.51 | IRPLVTQ | Fibrinogen |
| 806.37 | EYHTEK | Fibrinogen |
| 804.43 | AQLVDMK | Fibrinogen |
| 782.34 | DNTYNR | Fibrinogen |
| 781.38 | GADYSLR | Fibrinogen |
| 755.41 | VPPEWK | Fibrinogen |
| 718.37 | VSEDLR | Fibrinogen |
| 700.40 | DLLPSR | Fibrinogen |
| 673.31 | HQSACK | Fibrinogen |
| 658.30 | SSSYSK | Fibrinogen |
| 3817.65 | YQEDTCYGDAGSAFAVHDLE EDTWYATGILSFDK | Haptoglobin |
| 3292.52 | VDSGNDVTDIADDGCPKPPE IAHGYVEHSVR | Haptoglobin |
| 2848.30 | LPECEADDGCPKPPEIAHGY VEHSVR | Haptoglobin |
| 2679.39 | MVSHHNLTTGATLINEQWLL TTAK | Haptoglobin |
| 2115.04 | SPVGVQPILNEHTFCAGMSK | Haptoglobin |
| 1795.01 | VVLHPNYSQVDIGLIK | Haptoglobin |
| 1650.80 | YVMLPVADQDQCIR | Haptoglobin |
| 1458.73 | NLFLNHSENATAK | Haptoglobin |
| 1439.66 | TEGDGVYTLNNEK | Haptoglobin |
| 1311.61 | TEGDGVYTLNDK | Haptoglobin |
| 1290.73 | DIAPTLTLYVGK | Haptoglobin |
| 1288.62 | SCAVAEYGVYVK | Haptoglobin |
| 1273.63 | LPECEAVCGKPK | Haptoglobin |
| 1203.64 | VTSIQDWVQK | Haptoglobin |
| 1146.54 | HYEGSTVPEK | Haptoglobin |
| 987.54 | VMPICLPSK | Haptoglobin |
| 980.49 | VGYVSGWGR | Haptoglobin |
| 923.53 | ILGGHLDAK | Haptoglobin |
| 920.46 | GSFPWQAK | Haptoglobin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 895.47 | NPANPVQR | Haptoglobin |
| 858.49 | QLVEIEK | Haptoglobin |
| 809.38 | DYAEVGR | Haptoglobin |
| 760.40 | FTDHLK | Haptoglobin |
| 703.37 | VSVNER | Haptoglobin |
| 688.38 | QWINK | Haptoglobin |
| 688.38 | QWINK | Haptoglobin |
| 3954.02 | AIAANEADAVTLDAGLVYDA YLAPNNLKPVVAEFYGSK | Transferrin |
| 2401.08 | QQQHLFGSNVTDCSGNFCLF R | Transferrin |
| 2159.01 | IMNGEADAMSLDGGFVYIAG K | Transferrin |
| 2114.07 | SAGWNIPIGLLYCDLPEPR | Transferrin |
| 2070.03 | EDLIWELLNQAQEHFGK | Transferrin |
| 2014.91 | SDNCEDTPEAGYFAVAVVK | Transferrin |
| 1703.76 | EGTCPEAPTDECKPVK | Transferrin |
| 1632.83 | DCHLAQVPSHTVVAR | Transferrin |
| 1629.82 | EDPQTFYYAVAVVK | Transferrin |
| 1611.72 | IECVSAETTEDCIAK | Transferrin |
| 1592.72 | LCMGSGLNLCEPNNK | Transferrin |
| 1577.81 | TAGWNIPMGLLYNK | Transferrin |
| 1529.75 | KPVEEYANCHLAR | Transferrin |
| 1520.64 | FDEFFSEGCAPGSK | Transferrin |
| 1482.69 | DQYELLCLDNTR | Transferrin |
| 1478.73 | MYLGYEYVTAIR | Transferrin |
| 1419.73 | CGLVPVLAENYNK | Transferrin |
| 1417.65 | CSTSSLLEACTFR | Transferrin |
| 1358.70 | SVIPSDGPSVACVK | Transferrin |
| 1297.61 | DYELLCLDGTR | Transferrin |
| 1283.57 | EGYYGYTGAFR | Transferrin |
| 1276.63 | EFQLFSSPHGK | Transferrin |
| 1273.65 | HSTIFENLANK | Transferrin |
| 1260.57 | WCAVSEHEATK | Transferrin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1249.61 | SASDLTWDNLK | Transferrin |
| 1223.54 | CDEWSVNSVGK | Transferrin |
| 1195.55 | DSGFQMNQLR | Transferrin |
| 1166.59 | HQTVPQNTGGK | Transferrin |
| 1138.52 | WCALSHHER | Transferrin |
| 1000.50 | YLGEEYVK | Transferrin |
| 978.49 | DGAGDVAFVK | Transferrin |
| 964.53 | APNHAVVTR | Transferrin |
| 940.46 | ASYLDCIR | Transferrin |
| 878.46 | KPVDEYK | Transferrin |
| 874.44 | DSAHGFLK | Transferrin |
| 864.41 | DDTVCLAK | Transferrin |
| 830.39 | SCHTGLGR | Transferrin |
| 830.39 | SCHTAVGR | Transferrin |
| 827.40 | NPDPWAK | Transferrin |
| 735.40 | GDVAFVK | Transferrin |
| 686.33 | EACVHK | Transferrin |
| 663.38 | DLLFR | Transferrin |
| 654.31 | NTYEK | Transferrin |
| 652.30 | DSSLCK | Transferrin |
| 2455.15 | TSESGELHGLTTEEEFVEGI YK | Transthyretin |
| 2451.21 | ALGISPFHEHAEVVFTANDS GPR | Transthyretin |
| 2360.24 | YTIAALLSPYSYSTTAVVTN PK | Transthyretin |
| 1394.62 | AADDTWEPFASGK | Transthyretin |
| 1366.76 | GSPAINVAVHVFR | Transthyretin |
| 833.40 | GPTGTGESK | Transthyretin |
| 704.38 | VEIDTK | Transthyretin |
| 690.37 | CPLMVK | Transthyretin |
| 672.40 | VLDAVR | Transthyretin |

Other potentially contaminating peptides are the peptides listed in Table 4. These peptides, which can be attributed to various human keratins, were observed in the inventors' laboratory. The data were compiled from a total of 201 separate experiments using an ESI-LC-MS/MS system. Listed are the protein name, sequence, and number of experiments in which the peptide was observed, as well as how many total observations of the peptide were made. The number of observations listed is the sum of the number of times each peptide was observed at a charge state of +1H, +2H, and +3H combined for all experiments. In evaluating potential peptide targets, we take into account the number of times a peptide is observed within an experiment (which provides information about ionization efficiency and abundance) and how many times a peptide is observed among experiments (which indicates how a peptide is observed from experiment to experiment and reflects how enzyme cleavage is reproducible). The frequencies of observation in this table were used to generate the list of target peptides and subsequent antibodies used in Example I. From these results, we observed 118 total peptides. In the study shown in Example I, we've chosen a subset of these for the production of antibodies, starting with most observed peptides.

TABLE 4

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 2 | FLEQQNQVLQTK | 65 | 117 |
| Keratin 1 | QISNLQQSISDAEQR | 37 | 75 |
| Keratin 9 | DIENQYETQITQIEHEVSSSGQEVQSSAK | 29 | 67 |
| Keratin 1 | GSYGSGGSSYGSGGGSYGSGGGGGHGSYGSGSSSGGYR | 29 | 57 |
| Keratin 9 | GGSGGSHGGGSGFGGESGGSYGGGEEASGSGGYGGGSGK | 26 | 52 |
| Keratin 1 | WELLQQVDTSTR | 25 | 51 |
| Keratin 10 | ELTTEIDNNIEQISSYK | 23 | 66 |
| Keratin 1 | GGGGGGYGSGGSSYGSGGGSYGSGGGGGGR | 23 | 40 |
| Keratin 9 | VQALEEANNDLENK | 22 | 34 |
| Keratin 9 | EIETYHNLLEGGQEDFESSGAGK | 21 | 43 |
| Keratin 1 | SLNNQFASFIDK | 21 | 36 |
| Keratin 10 | GSLGGGFSSGGFSGGSFSR | 21 | 35 |
| Keratin 10 | ALEESNYELEGK | 21 | 25 |
| Keratin 1 | LNDLEDALQQAK | 20 | 39 |
| Keratin 9 | HGVQELEIELQSQLSK | 20 | 28 |
| Keratin 2 | YEELQITAGR | 20 | 21 |
| Keratin 1 | SLDLDSIIAEVK | 19 | 25 |
| Keratin 2 | TSQNSELNNMQDLVEDYKK | 17 | 19 |
| Keratin 9 | GGGGSFGYSYGGGSGGGFSASSLGGGFGGGSR | 16 | 20 |
| Keratin 1 | SGGGFSSGSAGIINYQR | 16 | 19 |
| Keratin 9 | SDLEMQYETLQEELMALK | 14 | 60 |
| Keratin 10 | NQILNLTTDNANILLQIDNAR | 14 | 25 |
| Keratin 9 | TLNDMRQEYEQLIAK | 14 | 17 |
| Keratin 1 | THNLEPYFESFINNLR | 12 | 19 |
| Keratin 1 | TNAENEFVTIKK | 12 | 14 |
| Keratin 10 | NVSTGDVNVEMNAAPGVDLTQLLNNMR | 11 | 21 |
| Keratin 10 | QSVEADINGLRR | 10 | 18 |
| Keratin 1 | SLNNQFASFIDKVR | 10 | 12 |
| Keratin 10 | NVQALEIELQSQLALK | 9 | 13 |
| Keratin 10 | QSLEASLAETEGR | 9 | 12 |
| Keratin 9 | NYSPYYNTIDDLKDQIVDLTVGNNK | 9 | 11 |
| Keratin 1 | TNAENEFVTIK | 9 | 9 |
| Keratin 10 | IRLENEIQTYR | 8 | 10 |
| Keratin 10 | SKELTTEIDNNIEQISSYK | 8 | 10 |
| Keratin 10 | LKYENEVALR | 8 | 9 |
| Keratin 10 | ADLEMQIESLTEELAYLK | 7 | 17 |
| Keratin 2 | IEISELNR | 7 | 7 |

TABLE 4-continued

All keratin peptides observed in 201 separate experiments
in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 1 | SLVNLGGSKSISISVAR | 7 | 7 |
| Keratin 1 | MSGECAPNVSVSVSTSHTTISGGGSR | 6 | 9 |
| Keratin 1 | FSSSGGGGSFGAGGGFGSR | 6 | 8 |
| Keratin 1 | LALDLEIATYR | 6 | 8 |
| Keratin 2 | VLYDAEISQIHQSVTDTNVILSMDNSR | 6 | 8 |
| Keratin 9 | LASYLDKVQALEEANNDLENK | 6 | 7 |
| Keratin 9 | QGVDADINGLR | 6 | 7 |
| Keratin 10 | TIDDLKNQILNLTTDNANILLQIDNAR | 6 | 7 |
| Keratin 10 | AETECQNTEYQQLLDIK | 6 | 6 |
| Keratin 9 | GGSGGSYGGGGSGGGYGGGSGSR | 6 | 6 |
| Keratin 2 | YLDGLTAER | 6 | 6 |
| Keratin 10 | DAEAWFNEK | 5 | 6 |
| Keratin 1 | NMQDMVEDYR | 5 | 6 |
| Keratin 2 | VDLLNQEIEFLK | 5 | 6 |
| Keratin 2 | GGGFGGGSSFGGGSGFSGGGFGGGGFGGGR | 5 | 5 |
| Keratin 10 | LENEIQTYR | 5 | 5 |
| Keratin 9 | QEYEQLIAK | 5 | 5 |
| Keratin 9 | TLLDIDNTR | 5 | 5 |
| Keratin 1 | NKLNDLEDALQQAK | 4 | 5 |
| Keratin 2 | NLDLDSIIAEVK | 4 | 5 |
| Keratin 2 | NVQDAIADAEQR | 4 | 5 |
| Keratin 9 | QVLDNLTMEK | 4 | 5 |
| Keratin 10 | QSVEADINGLR | 4 | 4 |
| Keratin 10 | SQYEQLAEQNR | 4 | 4 |
| Keratin 10 | LASYLDKVR | 3 | 4 |
| Keratin 1 | AEAESLYQSKYEELQITAGR | 3 | 3 |
| Keratin 1 | GSGGGSSGGSIGGR | 3 | 3 |
| Keratin 9 | SGGGGGGGLGSGGSIR | 3 | 3 |
| Keratin 2 | TAAENDFVTLKK | 3 | 3 |
| Keratin 1 | SKAEAESLYQSKYEELQITAGR | 3 | |
| Keratin 10 | ADLEMQIESLTEELAYLKK | 2 | 5 |
| Keratin 1 | LNDLEDALQQAKEDLAR | 2 | 4 |
| Keratin 2 | HGGGGGFGGGGFGSR | 2 | 3 |
| Keratin 1 | AEAESLYQSK | 2 | 2 |
| Keratin 1 | DYQELMNTK | 2 | 2 |
| Keratin 2 | FASFIDKVR | 2 | 2 |

TABLE 4-continued

All keratin peptides observed in 201 separate experiments
in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 2 | GFSSGSAVVSGGSR | 2 | 2 |
| Keratin 1 | GGSGGGGGGSSGGRGSGGGSSGGSIGGR | 2 | 2 |
| Keratin 10 | GSSGGGCFGGSSGGYGGLGGFGGGSFR | 2 | 2 |
| Keratin 9 | HGVQELEIELQSQLSKK | 2 | 2 |
| Keratin 10 | ISSSKGSLGGGFSSGGFSGGSFSR | 2 | 2 |
| Keratin 9 | MSCRQFSSSYLTSGGGGGGLGSGGSIR | 2 | 2 |
| Keratin 2 | MSGDLSSNVTVSVTSSTISSNVASK | 2 | 2 |
| Keratin 9 | MTLDDFR | 2 | 2 |
| Keratin 2 | NKLNDLEEALQQAK | 2 | 2 |
| Keratin 2 | QSGSRGGSGGGGSISGGGYGSGGGSGGR | 2 | 2 |
| Keratin 10 | SGGGGGGGGCGGGGGVSSLR | 2 | 2 |
| Keratin 2 | SISISVAGGGGGFGAAGGFGGR | 2 | 2 |
| Keratin 1 | TLLEGEESR | 2 | 2 |
| Keratin 10 | VLDELTLTK | 2 | 2 |
| Keratin 9 | EEMSQLTGQNSGDVNVEINVAPGK | 1 | 2 |
| Keratin 2 | MSCVARSGGAGGGACGFR | 1 | 2 |
| Keratin 9 | NHKEEMSQLTGQNSGDVNVEINVAPGK | 1 | 2 |
| Keratin 1 | FSSCGGGGSFGAGGGFGSRSLVNLGGSK | 1 | 1 |
| Keratin 9 | FSSSGGGGGGGRFSSSSGYGGGSSR | 1 | 1 |
| Keratin 1 | GGSGGGGGSSGGR | 1 | 1 |
| Keratin 1 | GGSGGGYGSGCGGGGGSYGGSGRSGR | 1 | 1 |
| Keratin 2 | GGSISGGGYGSGGGK | 1 | 1 |
| Keratin 2 | GGSISGGGYGSGGGKHSSGGGSR | 1 | 1 |
| Keratin 1 | GSSSGGVKSSGGSSSVR | 1 | 1 |
| Keratin 10 | HYSSSR | 1 | 1 |
| Keratin 9 | IGLGGRGGSGGSYGRGSR | 1 | 1 |
| Keratin 1 | LDSELKNMQDMVEDYR | 1 | 1 |
| Keratin 2 | LNDLEEALQQAK | 1 | 1 |
| Keratin 1 | LNVEVDAAPTVDLNR | 1 | 1 |
| Keratin 1 | LVVQIDNAK | 1 | 1 |
| Keratin 9 | NYSPYYNTIDDLK | 1 | 1 |
| Keratin 9 | QEIECQNQEYSLLLSIK | 1 | 1 |
| Keratin 9 | QFSSSYLSR | 1 | 1 |
| Keratin 2 | QLDSLLGERGNLEGELK | 1 | 1 |
| Keratin 1 | RSGGGGGRFSSCGGGGGSFGAGGGFGSR | 1 | 1 |
| Keratin 10 | RVLDELTLTK | 1 | 1 |
| Keratin 1 | SDLEAQVESLK | 1 | 1 |

TABLE 4-continued

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
| --- | --- | --- | --- |
| Keratin 10 | SEITELRR | 1 | 1 |
| Keratin 10 | SGGGGGGGGCGGGGGVSSLRISSSK | 1 | 1 |
| Keratin 1 | SMQDVVEDYK | 1 | 1 |
| Keratin 2 | STSSFSCLSR | 1 | 1 |
| Keratin 2 | TAAENDFVTLK | 1 | 1 |
| Keratin 1 | TGSENDFVVLKK | 1 | 1 |
| Keratin 10 | VTMQNLNDR | 1 | 1 |

In addition to the list of hypothetical tryptic peptides from abundant serum proteins that is shown in Table 5, the inventors have conducted experiments to identify peptides that are observed twice or more following actual tryptic digests of serum. Table 6 shows results from 29 separate experiments of tryptic digests of proteins from various sub-fractions of human serum run on ESI-LC-MS/MS.

TABLE 6

Commonly observed peptides from the most abundant serum proteins. Most common peptides observed among 29 separate experiments of tryptic digests of sub-fractions of human serum acquired by LC-MS/MS

| Protein name | Peptide sequence (SEQ ID NOS 580-677 disclosed respectively in order of appearance) | Number of Experiments | Number of Total Observations |
| --- | --- | --- | --- |
| Albumin | ALVLIAFAQYLQQCPFEDHVK | 3 | 3 |
| Albumin | AVMDDFAAFVEK | 14 | 17 |
| Albumin | DVFLGMFLYEYAR | 3 | 5 |
| Albumin | ETYGEMADCCAK | 2 | 2 |
| Albumin | FQNALLVR | 3 | 3 |
| Albumin | HPYFYAPELLFFAK | 2 | 3 |
| Albumin | KQTALVELVK | 2 | 2 |
| Albumin | KVPQVSTPTLVEVSR | 6 | 10 |
| Albumin | LDELRDEGK | 2 | 2 |
| Albumin | LVNEVTEFAK | 5 | 5 |
| Albumin | RHPDYSVVLLLR | 6 | 6 |
| Albumin | RHPYFYAPELLFFAK | 5 | 9 |
| Albumin | RPCFSALEVDETYVPK | 2 | 2 |
| Albumin | VFDEFKPLVEEPQNLIK | 4 | 15 |
| Albumin | VPQVSTPTLVEVSR | 3 | 4 |
| Albumin | YICENQDSISSK | 3 | 3 |
| Albumin | YLYEIAR | 5 | 5 |

TABLE 6-continued

Commonly observed peptides from the most abundant serum proteins.
Most common peptides observed among 29 separate experiments
of tryptic digests of sub-fractions of human serum
acquired by LC-MS/MS

| Protein name | Peptide sequence (SEQ ID NOS 580-677 disclosed respectively in order of appearance) | Number of Experiments | Number of Total Observations |
|---|---|---|---|
| Alpha-1-antitrypsin | AVLDVFEEGTEASAATAVK | 1 | 2 |
| Alpha-1-antitrypsin | AVLTIDEKGTEAAGAMFLEAIPMSIPPEVK | 1 | 10 |
| Alpha-1-antitrypsin | DLDSQTMMVLVNYIFFK | 1 | 2 |
| Alpha-1-antitrypsin | DTEEEDFHVDQATTVK | 5 | 5 |
| Alpha-1-antitrypsin | DTEEEDFHVDQVTTVK | 7 | 160 |
| Alpha-1-antitrypsin | DYNLNDILLQLGIEEAFTSK | 1 | 2 |
| Alpha-1-antitrypsin | ELDRDTVFALVNYIFFK | 3 | 3 |
| Alpha-1-antitrypsin | FNKPFVFLMIEQNTK | 3 | 9 |
| Alpha-1-antitrypsin | FNKPFVFLMIEQNTKSPLFMGK | 1 | 3 |
| Alpha-1-antitrypsin | FNRPFLMIIVPTDTQNIFFMSK | 2 | 8 |
| Alpha-1-antitrypsin | GTEAAGAMFLEAIPMSIPPEVK | 9 | 108 |
| Alpha-1-antitrypsin | GTHVDLGLASANVDFAFSLYK | 3 | 4 |
| Alpha-1-antitrypsin | ITPNLAEFAFSLYR | 8 | 24 |
| Alpha-1-antitrypsin | LQHLENELTHDIITK | 6 | 22 |
| Alpha-1-antitrypsin | LQHLVNELTHDIITK | 2 | 2 |
| Alpha-1-antitrypsin | LSITGTYDLK | 7 | 18 |
| Alpha-1-antitrypsin | LSITGTYDLKSVLGQLGITK | 2 | 2 |
| Alpha-1-antitrypsin | LSSWVLLMK | 2 | 6 |
| Alpha-1-antitrypsin | LYGSEAFATDFQDSAAAK | 3 | 4 |
| Alpha-1-antitrypsin | LYHSEAFTVNFGDTEEAK | 4 | 16 |
| Alpha-1-antitrypsin | LYHSEAFTVNFGDTEEAKK | 5 | 13 |
| Alpha-1-antitrypsin | SASLHLPKLSITGTYDLKSVLGQLGITK | 3 | 3 |
| Alpha-1-antitrypsin | SPLFMGK | 2 | 8 |
| Alpha-1-antitrypsin | SVLGQLGITK | 7 | 22 |
| Alpha-1-antitrypsin | SVLGQLGITKVFSNGADLSGVTEEAPLK | 2 | 2 |
| Alpha-1-antitrypsin | SVLGQLGITKVFSNGADLSGVTEEAPLKLSK | 2 | 2 |
| Alpha-1-antitrypsin | TLNQPDSQLQLTTGNGLFLSEGLK | 10 | 72 |
| Alpha-1-antitrypsin | VFSNGADLSGVTEEAPLK | 15 | 123 |
| Alpha-1-antitrypsin | VFSNGADLSGVTEEAPLKLSK | 4 | 17 |
| Alpha-1-antitrypsin | WERPFEVK | 2 | 2 |
| Apolipoprotein AI | AELQEGAR | 2 | 3 |
| Apolipoprotein AI | AKPALEDLR | 2 | 2 |
| Apolipoprotein AI | DLATVYVDVLK | 5 | 5 |
| Apolipoprotein AI | DLATVYVDVLKDSGR | 2 | 2 |
| Apolipoprotein AI | DLATVYVDVLKDSGRDYVSQFEGSALGK | 5 | 7 |

TABLE 6-continued

Commonly observed peptides from the most abundant serum proteins.
Most common peptides observed among 29 separate experiments
of tryptic digests of sub-fractions of human serum
acquired by LC-MS/MS

| Protein name | Peptide sequence (SEQ ID NOS 580-677 disclosed respectively in order of appearance) | Number of Experiments | Number of Total Observations |
|---|---|---|---|
| Apolipoprotein AI | DSGRDYVSQFEGSALGK | 9 | 29 |
| Apolipoprotein AI | DYVSQFEGSALGK | 16 | 73 |
| Apolipoprotein AI | EQLGPVTQEFWDNLEK | 16 | 168 |
| Apolipoprotein AI | EQLGPVTQEFWDNLEKETEGLR | 4 | 10 |
| Apolipoprotein AI | EQLGPVTQEFWDNLEKETEGLRQEMSK | 3 | 6 |
| Apolipoprotein AI | KWQEEMELYR | 1 | 4 |
| Apolipoprotein AI | LEALKENGGAR | 3 | 4 |
| Apolipoprotein AI | LHELQEK | 3 | 4 |
| Apolipoprotein AI | LLDNWDSVTSTFSK | 18 | 177 |
| Apolipoprotein AI | LREQLGPVTQEFWDNLEK | 7 | 20 |
| Apolipoprotein AI | LREQLGPVTQEFWDNLEKETEGLR | 5 | 17 |
| Apolipoprotein AI | LSPLGEEMR | 6 | 13 |
| Apolipoprotein AI | QGLLPVLESFK | 14 | 128 |
| Apolipoprotein AI | QLNLKLLDNWDSVTSTFSK | 2 | 2 |
| Apolipoprotein AI | THLAPYSDELR | 12 | 27 |
| Apolipoprotein AI | VEPLRAELQEGAR | 3 | 8 |
| Apolipoprotein AI | VKDLATVYVDVLK | 6 | 12 |
| Apolipoprotein AI | VKDLATVYVDVLKDSGR | 3 | 3 |
| Apolipoprotein AI | VKDLATVYVDVLKDSGRDYVSQFEGSALGK | 3 | 4 |
| Apolipoprotein AI | VQPYLDDFQK | 5 | 9 |
| Apolipoprotein AI | VQPYLDDFQKK | 2 | 4 |
| Apolipoprotein AI | VQPYLDDFQKKWQEEMELYR | 2 | 2 |
| Apolipoprotein AI | VSFLSALEEYTK | 15 | 169 |
| Apolipoprotein AI | VSFLSALEEYTKK | 4 | 7 |
| Apolipoprotein AI | WQEEMELYR | 12 | 29 |
| Apolipoprotein AII | EPCVESLVSQYFQTVTDYGK | 1 | 2 |
| Apolipoprotein AII | SKEQLTPLIK | 1 | 2 |
| Complement C3 | ILLQGTPVAQMTEDAVDAER | 1 | 3 |
| Haptoglobin | DIAPTLTLYVGK | 2 | 2 |
| Haptoglobin | GSFPWQAK | 3 | 3 |
| Haptoglobin | ILGGHLDAK | 1 | 3 |
| Haptoglobin | VGYVSGWGR | 3 | 4 |
| Haptoglobin | VTSIQDWVQK | 3 | 3 |
| Haptoglobin | VVLHPNYSQVDIGLIK | 3 | 4 |
| Transferrin | APNHAVVTR | 2 | 2 |

TABLE 6-continued

Commonly observed peptides from the most abundant serum proteins.
Most common peptides observed among 29 separate experiments
of tryptic digests of sub-fractions of human serum
acquired by LC-MS/MS

| Protein name | Peptide sequence (SEQ ID NOS 580-677 disclosed respectively in order of appearance) | Number of Experiments | Number of Total Observations |
|---|---|---|---|
| Transferrin | CLKDGAGDVAFVK | 2 | 2 |
| Transferrin | EDPQTFYYAVAVVK | 3 | 3 |
| Transferrin | IMNGEADAMSLDGGFVYIAGK | 3 | 3 |
| Transferrin | SKEFQLFSSPHGK | 2 | 2 |
| Transferrin | SMGGKEDLIWELLNQAQEHFGK | 1 | 3 |
| Transferrin | TAGWNIPMGLLYNK | 2 | 2 |
| Transthyretin | ALGISPFHEHAEVVFTANDSGPR | 5 | 6 |
| Transthyretin | RYTIAALLSPYSYSTTAVVTNPKE | 3 | 3 |
| Transthyretin | TSESGELHGLTTEEEFVEGIYK | 4 | 5 |
| Transthyretin | TSESGELHGLTTEEEFVEGIYKVEIDTK | 5 | 5 |
| Transthyretin | YTIAALLSPYSYSTTAVVTNPKE | 3 | 4 |

Any highly abundant and/or highly ionizable peptide derived from any of the mentioned high abundant/contaminating proteins and/or highly abundant serum proteins, or others, can be removed by a method of the invention. Such peptides include any of the peptides discussed herein. In addition, a skilled worker will recognize that suitable fragments or variants of these peptides can also be used to generate antibodies for the removal of highly abundant and/or ionizing peptides from a preparation for MS analysis, provided that the fragments or variants retain the epitope(s) of the starting peptides. Suitable fragments may lack between about 1-5 amino acids from one or both ends of the peptide. Suitable variants include, e.g., peptides having small substitutions, additions, deletions, etc. Peptides that exhibit at least about 90% (e.g., at least about 95%, or at least about 98%) sequence identity to one of the peptides are also included. Methods for determining if a peptide exhibits a particular percent identity to another peptide are conventional.

In one embodiment of the invention, a single antibody is designed that can bind specifically to two highly abundant and/or ionizing peptides. For example, if two of the peptides identified by a method of the invention map to adjacent positions in a protein, one can design an antigen that encompasses portions of each sequence for the generation of antibodies. At least some of the resulting antibodies will thus bind specifically to each of the two peptides.

It should be noted that a variety of methods of mass spectral analysis can be performed, using different forms of ionization. These include, e.g., electron ionization, chemical ionization (CI), electrospray ionization (ESI), matrix-assisted laser desorption/ionization (MALDI), inductively coupled plasma (ICP), glow discharge, fast atom bombardment (FAB), thermospray, desorption/ionization on silicon (DIOS), direct analysis in real time (ART), atmospheric pressure chemical ionization (APCI), secondary ion mass spectrometry (SIMS), thermal ionization, nanospray, corona discharge, atmospheric pressure MALDI (AP-MALDI), desorption electrospray ionization (DESI), and chemical ionization (CI).

Different sources of ionization can give rise to analytes (e.g. peptides) having different charges. For example, in ESI, peptides often exhibit multiple charges (e.g. +2H, +3H); whereas in MALDI, peptides almost exclusively have only a single charge. The manner in which analytes (e.g. peptides) receive their charge has an effect on the peptides that are observed. Some peptides ionize better by one method than the other, and vice versa. There is not 100% overlap between what is observed in MALDI vs. what is observed in ESI. In some cases, a peptide identified as being highly ionizing by one of these methods may not be observed with the other method. Therefore, it may be necessary in some cases to use antibodies against different peptides for MALDI as for ESI applications. However, because there is some overlap between targets identified by the ESI and MALDI methods, it may in some cases be possible to use the same antibodies for both MALDI and ESI applications. A skilled worker can readily determine which peptides (and antibodies thereto) are suitable for use for which type of ionization procedure. A method of the invention can be used to identify highly abundant and/or highly ionizable peptides for a variety of types of ionization, and a variety of types of mass spectrometry.

Samples from any biological source can be used for pre-processing a sample destined for MS analysis or for concentrating a peptide of interest, including humans or other animals, plants, viruses, etc., as well as non-biological materials that can be recognized by antibodies. A variety of types of cells, tissues, organelles etc. can serve as sources for samples for a method of the invention. These include, e.g., serum/plasma, cerebral spinal fluid, urine, cardiac tissue, tears, saliva, biopsy tissues or the like.

A skilled worker will recognize suitable highly abundant proteins whose removal would be beneficial for MS analysis from a given type of sample. For example:

For cardiac tissue, it would be beneficial to remove the component proteins of myofibrils and mitochondria.

For brain, spleen, liver, pancreas, glands and kidney, it would be beneficial to remove tubulin and cytoskeleton proteins and nuclear proteins.

For lung, stomach, intestines, esophagus, trachea, arteries, veins and bladder, it would be beneficial to remove connective tissue proteins (elastins, cytokeratins, extracellular matrix proteins and fibrin) in addition to tubulin, cytoskeletal proteins and nuclear lamins.

A "highly abundant" peptide, as used herein, is a peptide that is present at more than about 10% of total peptides/proteins in a digested sample, or in the case of peptides, peptides that are detected above about 20% relative intensity to other peptides within the spectrum of the same purified protein. In some embodiments of the invention, it may be desirable to remove a peptide that is present in a lower amount, but which is highly ionizable.

By "highly ionizable" is meant that the species is observed in the mass spectrometer at greater than about 20% relative signal intensity than other peptides. In one embodiment of the invention, the peptide is a proteotypic peptide. "Proteotypic peptides," as used herein, refers to peptides in a protein sequence that are most likely to be confidently observed by current MS-based proteomics methods, and are considered to be indicative of the presence of a particular protein. The terms "highly ionizable," "highly ionized," "highly ionizing," "high ionization efficiency," well-ionizing," etc. are used interchangeably herein. It is important to note that it is the unique combination of enzyme accessibility, the ionization method, and the specific amino acid residues which determine what peptides (e.g. highly ionized or proteotypic peptides) are observed. This can be instrument specific.

In peptide mixtures, especially those that are complex, peptides compete for ionization. While there is no 'absolute' measure of the ionization efficiency of a peptide used in this invention, a measure of the 'relative' ionization efficiency of one peptide vs. another peptide within a sample can be determined. Thus, when evaluating whether a particular peptide is highly ionizable or has a high ionization efficiency, and thus, should be a target of depletion by the current invention, the relative intensity as well as total number of observations of a peptide compared to others in a sample is recorded. In this invention, a peptide with a greater than about 20% relative signal intensity over the other peptides in a sample can be used as a "rule of thumb" to indicate that the peptide is "highly ionizable" and thus is likely to be a "proteotypic peptide" or a peptide that is most likely to be observed when the protein is digested by a protease and analyzed by mass spectrometry. Relative abundance is a universal measure used in virtually all mass spectrometry methods.

Peptides that are to be removed from a sample, or concentrated, by a method of the invention, can be of any suitable size, depending on a variety of factors, which will be evident to a skilled worker. For example, peptides to be contacted with an antibody (either for immunodepletion or concentration) should be of a size that is amenable to antibody binding. Such peptides can be, e.g., at least about 5-8 amino acids in length, e.g. about 5-20, or more, amino acids, or about 8-15 amino acids. As used herein, the term "about" refers to plus or minus 10%. For example, "about 8 amino acids" is 7-9 amino acids. A "range" of values, as used herein, includes the end points of the range. Thus, 5-8 includes both 5 and 8.

Although much of the present discussion is directed to the removal of protein or peptide contaminants before the analysis of a protein/peptide sample by MS, other potential types of contaminants can also be removed from such samples, provided that specific antibodies can be generated against the potential contaminants. Examples of highly ionizable contaminants that can be removed from samples prior to analysis of the samples by MS include, e.g., various polymers (such as detergents or preparation contaminants), lipids (e.g., highly negatively charged lipids), glycoproteins, carbohydrates, small molecules, peptoids, or metabolites.

Any of a variety of proteases (proteolytic enzymes, peptidases) can be used to digest a protein-containing sample in preparation for mass spectral analysis and/or for identifying highly abundant, well-ionizing and/or proteotypic peptides whose removal from a sample preparation for mass spectral analysis would be desirable. Generally, the protease is a site-specific protease that results in peptide fragments in an observable mass range for tandem MS mass spectrometers (about 500-about 7000 DA). The proteases can be selected from, e.g., serine proteases, threonine proteases, cysteine proteases, aspartic acid proteases (e.g., plasmepsis), metalloproteases, glutamic acid proteases, or combinations thereof. Suitable proteases include, e.g., the proteases shown in Table 1.

TABLE 1

Achromopeptidase
Aminopeptidase
Ancrod
Angiotensin Converting Enzyme
Bromelain
Calpain
Calpain I
Calpain II
Carboxypeptidase A
Carboxypeptidase B
Carboxypeptidase G
Carboxypeptidase P
Carboxypeptidase W
Carboxypeptidase Y
Caspase
Caspase 1
Caspase 2
Caspase 3
Caspase 4
Caspase 5
Caspase 6
Caspase 7
Caspase 8
Caspase 9
Caspase 10
Caspase 13
Cathepsin B
Cathepsin C
Cathepsin D
Cathepsin G
Cathepsin H
Cathepsin L
Chymopapain
Chymase
Chymotrypsin, a-
Clostripain
Collagenase
Complement C1r
Complement C1s
Complement Factor D
Complement factor I
Cucumisin
Dipeptidyl Peptidase IV
Elastase, leukocyte
Elastase, pancreatic
Endoproteinase Arg-C
Endoproteinase Asp-N
Endoproteinase Glu-C
Endoproteinase Lys-C
Enterokinase
Factor Xa
Ficin
Furin
Granzyme A
Granzyme B
HIV Protease
IGase
Kallikrein tissue

TABLE 1-continued

Leucine Aminopeptidase (General)
Leucine aminopeptidase, cytosol
Leucine aminopeptidase, microsomal
Matrix metalloprotease
Methionine Aminopeptidase
Neutrase
Papain
Pepsin
Plasmin
Prolidase
Pronase E
Prostate Specific Antigen
Protease, Alkalophilic from Streptomyces griseus
Protease from *Aspergillus*
Protease from *Aspergillus saitoi*
Protease from *Aspergillus sojae*
Protease (*B. licheniformis*) (Alkaline)
Protease (*B. licheniformis*) (Alcalase)
Protease from *Bacillus polymyxa*
Protease from *Bacillus* sp
Protease from *Bacillus* sp (Esperase)
Protease from *Rhizopus* sp.
Protease S
Proteasomes
Proteinase from *Aspergillus oryzae*
Proteinase 3
Proteinase A
Proteinase K
Protein C
Pyroglutamate aminopeptidase
Renin
Rennin
Streptokinase
Subtilisin
Thermolysin
Thrombin
Tissue Plasminogen Activator
Trypsin
Tryptase
Urokinase Among the commonly used proteases are: Endoproteinase Asp-N from a *Pseudomonas fragi* mutant; Endoproteinase Glu-C from *Staphylococcus aureus* V8; Endoproteinase Glu-C from *Staphylococcus aureus* V8; Endoproteinase Lys-C from *Lysobacter enzymogenes*; Endoproteinase Pro-C from *E. coli* BioChemika; Endoproteinase Pro-Pro-Y-Pro; Papain; Pepsin; Proteinase A (e.g. from *S. cerevisiae*); Proteinase K; Proteinase from *Bacillus licheniformis* Type VIII; α-Chymotrypsin; and Trypsin. See, e.g., the Sigma-Aldrich catalogue.

In one embodiment, one or more (up to all) of the following proteases are used: trypsin, chymotrypsin, lys-C, or combinations thereof.

Antibodies specific for a peptide that is obtained by digesting a potentially contaminating protein by one method (e.g., trypsin digestion) may or may not recognize the same epitope(s) in peptides obtained by digesting the protein by another method (e.g., with a protease that recognizes a different cleavage site). Therefore, in one embodiment, in which highly abundant and/or ionizable and/or proteotypic peptides have been identified from a digest of a protein with an enzyme, that enzyme is also used to digest a sample for mass spectrometry (from which it is desirable to remove undesirable highly abundant and/or ionizable peptides).

In one embodiment, a protein target that has been selected for removal from a sample is cleaved to peptides by more than one method (e.g. digested, in separate reactions, with different proteases), and the presence of highly ionizable peptides is determined for peptides from each of the digests. Particularly desirable peptides may be obtained from one or more of the digests.

Chemical methods for cleaving proteins to peptides can also be used, and are well-known in the art. Suitable methods include, e.g., cleavage at aspartyl residues by formic acid; cyanogen bromide cleavage; 2-iodosobenzoic acid cleavage (IBA, e.g. using 2-Nitro-5-thiocyanatobenzoic acid powder), etc.

Once candidate peptides are identified (and verified) whose removal would be beneficial, these peptides can be physically removed from samples by any of a variety of conventional methods that involve agents (e.g. chemical agents) which are specific for the peptides. For example, peptoids, or small molecules with high affinities (e.g., clickity-click chemistries using highly functionalized peptoid oligomers, etc.) can be bound to agents that are specific for them and can thus be subsequently removed from the initial sample.

In one embodiment, the peptides are removed by immunodepletion, using antibodies that are specific for the peptides. For example, immunoprecipitation, or various forms of affinity products, including affinity chromatography, nanocolumns, spin columns, adsorption to antibody coated surfaces, such as pipette tips (e.g. disposable pipette tips), filters, membranes, etc. can be used.

An antibody that is "specific for" a peptide refers to an antibody that preferentially recognizes a defined sequence of amino acids, or epitope, that is present in the peptide, and not generally other peptides unintended for binding to the antibody. An antibody that "binds specifically" to ("is specific for"; binds "preferentially" to) a peptide of the invention interacts with the antibody, or forms or undergoes a physical association with it, in an amount and for a sufficient time to allow the peptide to be removed from the solution, or to be captured from the solution, by a method of the invention. By "specifically" or "preferentially" is meant that the antibody has a higher affinity, e.g. a higher degree of selectivity, for such a peptide than for other peptides in a sample. For example, the antibody can have an affinity for the peptide of at least about 5-fold higher than for other peptides in the sample. Typically this is application specific. For example, it does not matter if the antibody cross-reacts with peptides from proteins of different samples, if those peptides are not present in the sample of interest. The affinity or degree of specificity can be determined by a variety of routine procedures, including, e.g., competitive binding studies. A "cognate" peptide, as used herein, is a peptide for which an antibody is specific.

Methods for producing specific antibodies against a peptide of interest and for purifying the peptides are conventional. The peptides used for generation of the antibodies can be produced by a variety of methods, including isolating them from purified proteins that have been cleaved with a suitable enzymatic or chemical method. Alternatively, the peptides can be produced using conventional chemical synthesis techniques, such as those described, e.g., in G. Barony et al., The Peptides: Analysis, Synthesis & Biology, Academic Press, pp. 3-285 (1980). Some chemically synthesized peptides can be obtained from commercial suppliers. Alternatively, a peptide of the invention can be produced recombinantly following conventional genetic engineering techniques.

Generally, a peptide against which antibodies are to be produced is isolated or substantially purified before it is used to stimulate antibody formation. The term "substantially purified," as used herein refers to a molecule, such as a peptide, that is substantially free of other proteins, peptides, lipids, carbohydrates, nucleic acids and other biological materials with which it is naturally associated. For example, a substantially pure compound, such as a peptide, can be at least about 60%, by dry weight, preferably at least about 70%, 80%, 90%, 95%, or 99% the molecule of interest. Methods for isolating (purifying) proteins or peptides are conventional.

An "antibody," as used herein, can be, e.g., polyclonal, monoclonal (mAb), recombinant, humanized or partially humanized, chimeric, single chain, Fab, or fragments of such antibodies. Other specific binding partners, such as aptamers, can also be used. The antibody can be of any isotype, e.g., IgM, various IgG isotypes such as $IgG_1$' $IgG_{2a}$, etc., and it can be from any animal species that produces antibodies, including goat, rabbit, mouse, chicken or the like. A mixture of antibody types can be used. It is noted that antibodies raised against purified peptides, even polyclonal antibodies, will exhibit high degrees of specificity for a cognate peptide.

Antibodies can be prepared according to conventional methods, which are well known in the art. See, e.g. Green et al, Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections. 2.5.1-2.6.7; and Harlow et al., Antibodies: A Laboratory Manual, page 726 (Cold Spring Harbor Laboratory Pub. 1988). Methods of preparing humanized or partially humanized antibodies, antibody fragments, etc. and methods of purifying antibodies, are conventional.

In one embodiment, a mixture of antibodies is used which, in total, are specific for most, if not all, of the potentially contaminating peptides whose removal will bring about a significantly reduced amount of background. The number of proteins/peptides to be removed can be determined empirically, e.g. using methods as described herein. Generally, the removal of peptides from about 1-20 (e.g., about 8-12) proteins from a sample results in a significantly reduced amount of background. The removal of about 2-8 (e.g. about 3-5) peptides from each of the proteins is generally sufficient. In one embodiment, in a sample that contains keratin as a contaminant, the removal of about 2-6 keratin peptides (e.g., about 2-3 or about 4-6 such peptides) results in a significantly reduced amount of background. In another embodiment, in a sample from serum and/or plasma, the removal of peptides from about 2-14 highly abundant proteins (e.g., from about 10-14 such proteins, or about 2-7 such proteins, can result in a beneficial effect. In one embodiment, the removal of even one peptide from even one portion of the chromatograph can achieve a beneficial effect, allowing other species to be observed.

In general, immunodepletion of peptides according to the invention is carried out by contacting the peptides in a sample with specific antibodies under conditions that are effective for the antibodies to bind specifically to the peptides (to form specific antigen (peptide)-antibody complexes). "Effective conditions" vary according to a variety of factors, including the affinity of the antibodies for the peptides, components of the binding mixture, etc. Effective conditions can be optimized empirically, by conventional, routine procedures, as set forth, e.g., in Current Protocols in Immunology (Coligan et al., editors, John Wiley & Sons, Inc).

The antibodies may be free floating in the sample solution. After binding specifically to its cognate peptide, such an antibody can be separated from the sample solution by a variety of methods, which will be evident to a skilled worker. For example, the complexes may be allowed to bind to secondary antibodies which, in turn, are attached to a solid surface, to a magnetic bead, etc., so that the complex can be readily removed from the sample. Other separation techniques include, e.g., precipitation, centrifugation, filtration, chromatography, or the use of magnetism.

In another embodiment of the invention, an antibody that is specific for a peptide of interest is attached to (immobilized on) a surface; and the surface provides a mechanism by which peptides bound to antibodies thereon can be separated from the sample solution.

Any of a variety of suitable, compatible surfaces can be used in conjunction with this invention. The surface (usually a solid, preferably a suitable rigid or semi-rigid support) can be any of a variety of organic or inorganic materials or combinations thereof, including, merely by way of example, plastics such as polypropylene or polystyrene; ceramic; silicon; (fused) silica, quartz or glass, which can have the thickness of, for example, a glass microscope slide or a glass cover slip; paper, such as filter paper; diazotized cellulose; nitrocellulose filters; nylon membrane; or polyacrylamide gel pad. Suitable surfaces include membranes, filters, chips, slides, wafers, fibers, magnetic or nonmagnetic beads, gels, tubing, plates, polymers, microparticles, capillaries, or the like. The substrate can have a variety of surface forms, such as wells, trenches, pins, channels and pores, to which the nucleic acid probes are bound. The shape of the surface is not critical. It can, for example, be a flat surface such as a square, rectangle, or circle; a curved surface; or a three dimensional surface such as a bead, particle, strand, precipitate, tube, sphere, etc. Microfluidic devices are also encompassed by the invention.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the antibody bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

Solid phase devices that can be used in conjunction with methods of the invention include a variety of affinity products, e.g., microtiter plates; flow-through assay devices; dipsticks; immunocapillary or immunochromatographic devices; disposable pipette tips for specific target(s), in either single or multiplex format; spin columns; filter plates or membranes; chromatography columns; affinity columns/plates; nanocolumns; online filters for online or offline chromatography; dedicated sample processing instrumentation; pre-columns for HPLC and nano-HPLC instrumentation that are coupled directly to mass spectrometers; etc.

In one embodiment, the antibodies are in the form of an array. The term "array" as used herein means an ordered arrangement of addressable, accessible, spatially discrete or identifiable, molecules (e.g., antibodies) disposed on a surface. Arrays can comprise any number of sites that comprise probes, from about 5 to, in the case of a microarray (sometimes referred to herein as a "chip"), tens to hundreds of thousands or more.

Immobilization of an antibody of the invention on a surface can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the antibody having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the antibody, such as 6-aminohexanoic acid, and the component is then avidin, streptavidin or an analogue thereof. An alternative is a situation in which the moiety has the amino acid sequence His-His-His-His-His-His (SEQ ID NO:703) and the carrier comprises a Nitrilotriacetic Acid derivative (NTA) charged with $Ni^{++}$ ions.

Procedures for separating peptides bound to antibodies on such surfaces from a sample will be evident to a skilled worker. For example, beads containing bound peptides can be spun out of a solution, or if they are magnetic, removed with a magnet. A sample can be placed on a chip and removed; and peptides bound to their cognate antibodies on the chip will remain behind. Samples can be passed through columns to which the antibodies are bound, spun through spin columns containing the antibodies, or passaged through pipette tips to which the antibodies are bound.

Antibodies of the invention can also be used with detectors if specific isoforms of proteins are desired to be observed.

As noted, another embodiment of the invention is a method to detect a protein of interest (e.g. a disease marker, a protein component of a pathogen, or a protein that is produced by a pathogen during infection or by the host in response to infection by the pathogen). In such a method, one or more highly ionizable peptides from the protein of interest are identified and purified, and antibodies specific for these peptides are generated, all as described elsewhere herein.

In one embodiment of the invention, the method comprises obtaining a sample (e.g. a bodily fluid or tissue suspected of containing a pathogen) from a subject; cleaving proteins in the sample to peptides; and contacting the resulting peptides with antibodies of the invention, under conditions effective for the formation of a specific antigen (peptide)-antibody reactions. Following the binding of the antibodies to the peptides (thereby isolating, concentrating, enriching, capturing the peptides), excess components of the sample are optionally removed (washed off); the bound peptides are eluted, using conventional procedures; and the eluted peptides are analyzed by mass spectrometry. The detection of peptides from organisms of interest can be used for medical diagnosis, monitoring the environment, analysis of samples suspected of being involved in bioterrorism, or a variety of other uses that will be evident to a skilled worker.

Another embodiment of the invention involves the detection of disease markers (proteins) that are present in low levels in a sample. Highly ionizable peptides from such markers are captured and eluted as described above for pathogen-specific peptides. By identifying highly ionizable peptides from these markers and capturing them with an antibody specific for the peptides, one can significantly increase the sensitivity of detection of the markers in an MS assay. It is thus possible to diagnose a disease (to detect the presence of such disease markers in a sample from a subject), in spite of low levels of the markers of the disease.

Another aspect of the invention is a composition comprising highly abundant and/or ionizable and/or proteotypic peptides of the invention. Such a composition can be used to generate antibodies that are specific for the peptides. Another aspect of the invention is a composition comprising antibodies that are specific for the highly abundant and/or ionizable and/or proteotypic peptides of the invention. The antibodies may be of any of the types discussed herein, or combinations thereof.

Another aspect of the invention is a kit for carrying out any of the methods of the invention. For example, one embodiment is a kit for immunodepleting undesired peptides from a sample destined to be subjected to MS analysis. Another embodiment is a kit for detecting (diagnosing) the presence of peptides of interest (e.g., highly ionizing peptides from proteins from one or more pathogens, or from a disease marker) in a sample. A kit of the invention may, for example, comprise one or more antibodies that are specific for such and, optionally, means for storing or packaging the antibodies. The antibodies may be in a lyophilized form or in liquid form; they may be stabilized.

The components of the kit will vary according to which method is being performed. Optionally, the kits comprise instructions (e.g., written instructions) for performing the method. Other optional elements of a kit of the invention include suitable buffers, media components, or the like; containers; or packaging materials. The reagents of the kit may be in containers in which the reagents are stable, e.g., in lyophilized form or stabilized liquids. The reagents may also be in single use form, e.g., in amounts for depleting peptides from a single sample, or for carrying out a single diagnostic test. Other components of a kit can easily be determined by one of skill in the art. Such components may include suitable controls or standards, buffers or other reagents appropriate for constituting a reaction medium allowing the formation of a peptide-antibody complex, etc.

Another aspect of the invention is a device to which one or more antibodies of the invention are attached. Such a device can be used to immunodeplete one or more (e.g. about 5 or more) peptides from a sample, or to isolate/concentrate one or more (e.g. about 5 or more) peptides of interest. Any of the types of devices discussed herein are included.

A skilled worker will recognize that the methods, compositions and devices of the invention can be applied to a wide range of uses, including, e.g., diagnostics, clinical assays, toxicology, glycomics, lipidomics, etc.

In the foregoing and in the following examples, all temperatures are set forth in uncorrected degrees Celsius; and, unless otherwise indicated, all parts and percentages are by weight.

EXAMPLES

Example 1

Immunodepletion of Keratin Peptides from a Sample

Antibodies against two keratin-specific peptides were used to immunodeplete a sample containing a mixture of purified peptides. The purified peptides used in the experiment were the same as the antigens used for antibody production and were designed to be representative of two distinct regions in the sequence of Keratin 1 and Keratin 2. The peptide named Keratin Peptide 1 (KP1), (CSISDAEQRGENALK, MW=1621 Da) (SEQ ID NO:704), was designed to represent amino acids 424-437 of Keratin 1 and 430-436 of Keratin 2. The peptide named Keratin Peptide 2 (KP2), (ELLQQVDTSTR, MW=1290 Da) (SEQ ID NO:705) was designed to represent amino acids 212-222 of Keratin 1 and 217-227 of Keratin 2.

The peptides were synthesized chemically and polyclonal antibodies were raised against each peptide, using conventional procedures. We conducted ELISA assays, using conventional procedures, which confirmed that the antisera raised against each of these peptides do, in fact, bind to their cognate peptides specifically. The disposable pipette tips used for this experiment were loaded with cellulose that was pretreated with potassium iodate (KIO3). The tips were washed with ammonium bicarbonate, 20 mM, pH 7.4, 20 mM Octyl-B-D-Glycopyranoside once. The antibody was chemically bound to the column in the same buffer, blocked with a protein-free blocker, then washed three times with the buffer. The peptide mixtures were prepared in the same buffer and then loaded onto the antibody-bound pipette tips. Samples were aspirated five times to bind the peptides. The unbound sample was then analyzed by MALDI-TOF MS, using conventional procedures.

Figure 3:
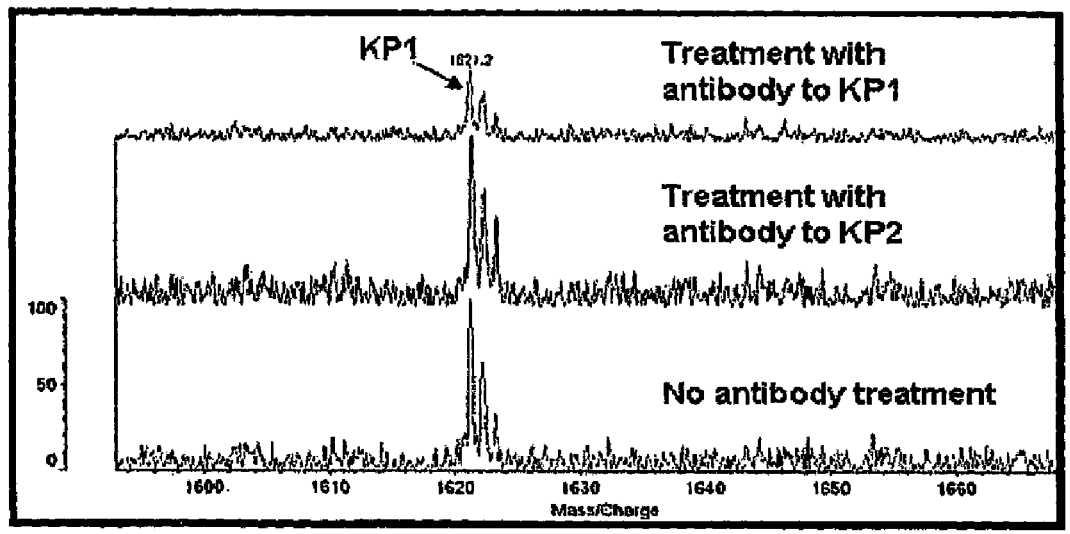
FIG. 3 shows MALDI spectra showing the specificity of antibodies against two peptides from keratin.

To demonstrate the specificity of the two antibodies for their cognate peptides, samples containing just KP1 were subjected to treatment with pipette tips loaded with antibodies against KP1 or KP2 and the unbound fraction was analyzed by MALDI-TOF MS. As shown in FIG. 3, each antibody exhibited the desired specificity. The bottom spectrum of the figure is a control showing 2 ng of KP1 loaded onto the sample plate. The middle spectrum shows the sample after treatment with an antibody tip to KP2. Note no loss in signal intensity of the KP1 peak, as the KP2 antibody does not bind to KP1. The top spectrum shows the sample after treatment with the antibody to KP1. Note the loss in signal intensity of the KP1 peak due the removal of KP1 from the sample by the antibody tip to KP1.

Figure 4:
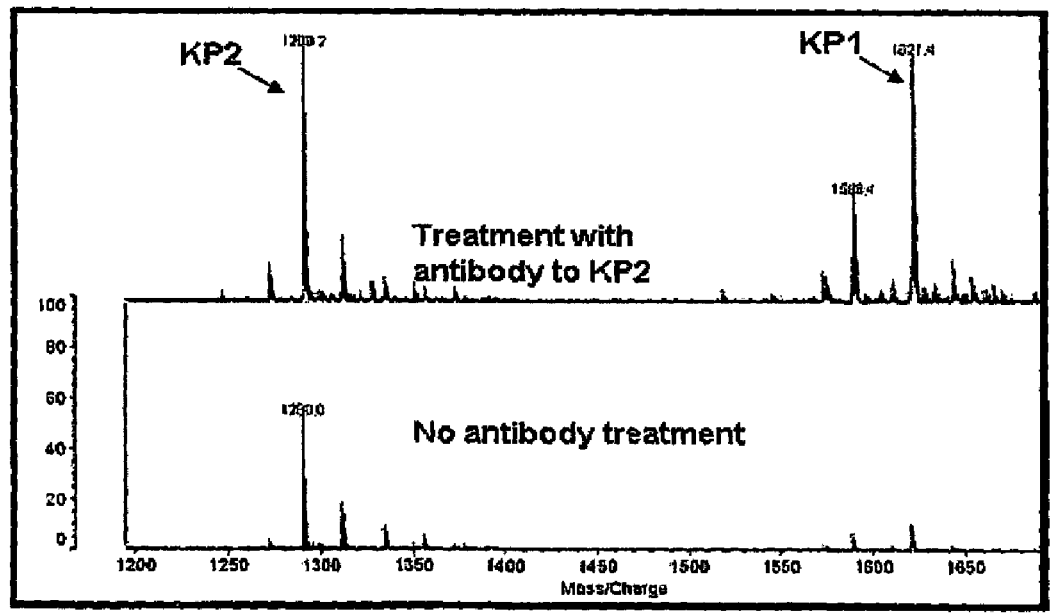
FIG. 4 shows MALDI spectra showing the benefits of immunodepletion of keratin peptides from a sample.

To demonstrate the beneficial effect of treating a sample with antibodies against keratin-specific peptides, samples containing both purified KP1 and KP2 were treated by a method of the invention, as above. FIG. 4 shows the beneficial effects of the method. The bottom spectrum shows a mixture of equal amounts (200 ng each) of the two keratin peptides (KP1 and KP2) without having been treated with the tips bound with antibodies. Note that when equal amounts of KP1 and KP2 are analyzed (bottom spectrum), KP2 is detected at a higher relative intensity. This is due to the fact that KP2 has a higher ionization efficiency than KP1. The top spectrum shows the result after treatment of the sample with an antibody tip against KP2. After treatment, as shown in the top spectrum, the relative intensity of KP1 is much higher than before treatment. This is attributed to the fact that there is less KP2 in the sample, thus allowing better detection of KP1.

Example II

Immunodepletion of Highly Abundant Peptides from a Serum Sample

To select suitable peptides for immunodepletion, we first identified the most highly abundant proteins in serum, as shown in Table 5. We then performed an "in silico" digest of these serum proteins, using cleavage specific sites for trypsin. This provided a total of all of the possible peptides from a tryptic digest. We then looked for these peptides using ESI— liquid chromatography mass spectrometry in samples derived from the tryptic digestion of sub-fractions of human serum. We determined how many times each peptide was observed experimentally, determined their ionizing efficiencies, and determined which peptides were proteotypic under these conditions. On the basis of these analyses, we selected the top 2-4 peptide sequences corresponding to the highest number of observations (Table 7). We will generate antibodies against these 24 peptides, combine the antibodies in a depletion column (an affinity column, using cellulose as the matrix material), pass tryptic digests of serum samples over the column, and collect the eluate (which will have been immunodepleted for the 24 peptides). All of these procedures will be carried out with conventional procedures. Following depletion of high-abundance peptides, we expect that novel peptides will be observed during MS as compared to undepleted control samples. Furthermore, peptides corresponding to proteins that are non-specifically depleted by whole-protein affinity column approaches (e.g. MARS, IgY12) will be observed by this peptide-based depletion method. Consequently, this method will eliminate the loss of peptides which are removed by the whole-protein removal approaches, either because they bind to the proteins that are targeted for removal or because they bind non-specifically to the affinity columns.

TABLE 7

| Protein name | Peptide sequence (SEQ ID NOS 678-702 disclosed respectively in order of appearance) | Number of Experiments | Number of Total Observations |
| --- | --- | --- | --- |
| Albumin | VFDEFKPLVEEPQNLIK | 4 | 15 |
| Albumin | RHPYFYAPELLFFAK | 5 | 9 |
| Albumin | KVPQVSTPTLVEVSR | 6 | 10 |
| Albumin | AVMDDFAAFVEK | 14 | 17 |
| Alpha-1-antitrypsin | DTEEEDFHVDQVTTVK | 7 | 160 |
| Alpha-1-antitrypsin | ITPNLAEFAFSLYR | 8 | 24 |
| Alpha-1-antitrypsin | GTEAAGAMFLEAIPMSIPPEVK | 9 | 108 |
| Alpha-1-antitrypsin | TLNQPDSQLQLTTGNGLFLSEGLK | 10 | 72 |

TABLE 7-continued

| Protein name | Peptide sequence (SEQ ID NOS 678-702 disclosed respectively in order of appearance) | Number of Experiments | Number of Total Observations |
|---|---|---|---|
| Alpha-1-antitrypsin | VFSNGADLSGVTEEAPLK | 15 | 123 |
| Apolipoprotein AI | QGLLPVLESFK | 14 | 128 |
| Apolipoprotein AI | VSFLSALEEYTK | 15 | 169 |
| Apolipoprotein AI | DYVSQFEGSALGK | 16 | 73 |
| Apolipoprotein AI | EQLGPVTQEFWDNLEK | 16 | 168 |
| Apolipoprotein AI | LLDNWDSVTSTFSK | 18 | 177 |
| Apolipoprotein AII | EPCVESLVSQYFQTVTDYGK | 1 | 2 |
| Apolipoprotein AII | SKEQLTPLIK | 1 | 2 |
| Complement C3 | ILLQGTPVAQMTEDAVDAER | 1 | 3 |
| Haptoglobin | VGYVSGWGR | 3 | 4 |
| Haptoglobin | VVLHPNYSQVDIGLIK | 3 | 4 |
| Transferrin | SMGGKEDLIWELLNQAQEHFGK | 1 | 3 |
| Transferrin | EDPQTFYYAVAVVK | 3 | 3 |
| Transferrin | IMNGEADAMSLDGGFVYIAGK | 3 | 3 |
| Transthyretin | TSESGELHGLTTEEEFVEGIYK | 4 | 5 |
| Transthyretin | ALGISPFHEHAEVVFTANDSGPR | 5 | 6 |
| Transthyretin | TSESGELHGLTTEEEFVEGIYKVEIDTK | 5 | 5 |

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above (including U.S. provisional application 60/818,363, filed Jul. 3, 2006) and in the figures, are hereby incorporated in their entirety by reference.

We claim:

1. A method for pre-processing a sample for mass spectral analysis, comprising cleaving proteins in the sample to peptides and immunodepleting highly abundant and/or well-ionizing and/or proteotypic peptides from the sample.

2. The method of claim 1, wherein the mass spectral analysis is matrix-assisted laser desorption/ionization spectroscopy (MALDI).

3. The method of claim 1, wherein the mass spectral analysis is electrospray ionization mass spectroscopy (ESI).

4. The method of claim 1, wherein the cleaving comprises digesting the proteins with a protease.

5. The method of claim 4, wherein the protease is trypsin, chymotrypsin, and/or Lys-C.

6. The method of claim 1, wherein the cleaving is achieved with a chemical method.

7. The method of claim 6, wherein the chemical method is formic acid cleavage, cyanogen bromide cleavage and/or 2-iodosobenzoic acid (IBA) cleavage.

8. The method of claim 1, wherein peptides from between about 1-20 proteins are removed from the sample.

9. The method of claim 1, wherein peptides from between about 8-12 proteins are removed from the sample.

10. The method of claim 1, wherein the sample is from plasma/serum, and the high abundant and/or well-ionizing and/or proteotypic peptides are from one or more of the proteins listed in Table 5.

11. The method of claim 10, wherein the highly abundant and/or well-ionizing and/or proteotypic peptides comprise one or more of the peptides listed in Table 3 and/or Table 6 and/or Table 7.

12. The method of claim 1, wherein the sample contains keratins and/or trypsin, and the high abundant and/or well-ionizing and/or proteotypic peptides are selected from one or more of the peptides listed in Table 2 and/or Table 4.

13. The method of claim 8, wherein about 3-5 peptides from each of the proteins are removed.

14. The method of claim 1, wherein the immunodepletion is carried out by contacting the sample comprising cleaved proteins with one or more antibodies that are specific for highly abundant and/or well-ionizing and/or proteotypic peptides in the sample, under conditions that are effective for the antibodies to bind specifically to their cognate peptides, and separating the resulting antibody/peptide complexes from the sample.

15. The method of claim 14, further wherein the well-ionizing peptides are identified by a) cleaving a protein known or suspected to be a contaminant with a protease or a chemical method; b) subjecting the resulting peptides to mass spectrometry; c) ranking the peptides in order of degree of ionization.

16. The method of claim 14, wherein one or more of the antibodies are monoclonal antibodies.

17. The method of claim 14, wherein all of the antibodies are monoclonal antibodies.

18. The method of claim 14, wherein one or more of the antibodies are polyclonal antibodies.

19. The method of claim 14, wherein all of the antibodies are polyclonal antibodies.

* * * * *